United States Patent
Koskinen et al.

(10) Patent No.: US 8,936,655 B2
(45) Date of Patent: Jan. 20, 2015

(54) INTEGRATED PROCESS SYSTEM FOR SINGLE CELL OIL PRODUCTION AND A PULP AND/OR PAPER INDUSTRY PROCESS

(75) Inventors: Perttu Koskinen, Helsinki (FI); Reijo Tanner, Hikia (FI)

(73) Assignee: Neste Oil Oyj, Espoo (FI)

( * ) Notice: Subject to any disclaimer, the term of this patent is extended or adjusted under 35 U.S.C. 154(b) by 462 days.

(21) Appl. No.: 13/333,203

(22) Filed: Dec. 21, 2011

(65) Prior Publication Data

US 2012/0159840 A1    Jun. 28, 2012

Related U.S. Application Data

(60) Provisional application No. 61/459,964, filed on Dec. 22, 2010.

(30) Foreign Application Priority Data

Dec. 22, 2010 (EP) .................................. 10196494

(51) Int. Cl.
*C10L 1/00* (2006.01)
*C12P 7/64* (2006.01)
(Continued)

(52) U.S. Cl.
CPC ................. *C12P 7/64* (2013.01); *C12N 9/2434* (2013.01); *C12P 21/02* (2013.01); *D21C 5/005* (2013.01); *D21H 11/20* (2013.01); *Y02E 50/13* (2013.01)
USPC ............. 44/307; 435/134; 435/183; 435/189; 435/195; 435/232; 435/233

(58) Field of Classification Search
USPC ............ 44/307, 385; 435/183, 189, 193, 195, 435/232, 233, 134
See application file for complete search history.

(56) References Cited

U.S. PATENT DOCUMENTS

| 7,691,792 B1 | 4/2010 | Fisher et al. |
| 2009/0011480 A1 | 1/2009 | Trimbur et al. |

(Continued)

FOREIGN PATENT DOCUMENTS

| EP | 1396531 | 3/2004 |
| EP | 1398364 | 3/2004 |

(Continued)

OTHER PUBLICATIONS

Szczesna-Antczak et al., "Relationsihps between lipases and lipids in mycelia of two Mucor strains", Enzyme and Microbial Technology, 2006, 29:1214-1222.

(Continued)

*Primary Examiner* — Cephia D Toomer
(74) *Attorney, Agent, or Firm* — Andrus Intellectual Property Law, LLP

(57) ABSTRACT

The present invention relates to an integrated process, which comprises a single cell oil production process, and a pulp and/or paper industry process. The process comprises that in the single cell oil production process is used a microorganism capable of producing lipids or lipids and enzymes when cultivated on a medium comprising organic material from pulp and/or paper industry. Lipids or lipids and enzymes are produced by said microorganisms in the single cell oil production process and/or in a process connected into it. The present invention relates also to use of lipids produced in the process as biofuel or as a component of biofuel or as a starting material for biofuel production and use of enzymes produced in the lipid production process in pulp and/or paper industry or in other applications as an enzyme preparation or as a source of enzymes.

17 Claims, 7 Drawing Sheets

(51) Int. Cl.
*C12N 9/42* (2006.01)
*C12P 21/02* (2006.01)
*D21C 5/00* (2006.01)
*D21H 11/20* (2006.01)

(56) References Cited

U.S. PATENT DOCUMENTS

| | | | |
|---|---|---|---|
| 2009/0064567 | A1 | 3/2009 | Lippmeier |
| 2009/0165968 | A1 | 7/2009 | Tan et al. |
| 2009/0217569 | A1* | 9/2009 | Pastinen et al. ............ 44/308 |

FOREIGN PATENT DOCUMENTS

| | | |
|---|---|---|
| EP | 1741767 | 1/2007 |
| EP | 1741768 | 1/2007 |
| WO | 9203541 | 3/1992 |
| WO | 2007091231 | 8/2007 |
| WO | 2009035551 | 3/2009 |
| WO | 2009063138 | 5/2009 |
| WO | 2010042842 | 4/2010 |

OTHER PUBLICATIONS

International Search Report for PCT/FI2011/051136 dated May 3, 2012.
Written Opinion for PCT/FI2011/051136 dated May 3, 2012.
Aachary et al., "Corncob-induced endo-1,4-beta-D-Xylanase of *Aspergillus oryzae* MTCC 5154: Production and characterization of Xylobiose from Glucuronoxylan", J. Agric. Food Chem., 2008, 56:3981-3988.
Bajpai, "Biological Bleaching of Chemical Pulps", Critical Reviews in Biotechnology, 2004, 24(1):1-58.
Beg et al., "Microbial xylanases and their industrial applications: a review", Appl. Microbiol. Biotechnol, 2001, 56:326-338.
Bhat, "Cellulases and related enzymes in biotechnology", Biotechnology Advances, 2000, 18:355-383.
Chipeta et al., "Effect of cultivation pH and agitation rate on growth and xylanase production by *Aspergillus oryzae* in spent sulphite liquor", J. Ind. Microbiol. Biotechnol., 2008, 35:587-594.
Dhiman et al., "Industrial applications and future prospects of microbial xylanases: A review", BioResources, 2008, 3 (4):1377-1402.
Fall et al., "Bioconversion of Xylan to Triglycerides by Oil-Rich Yeasts", Applied and Environmental Microbiology, 1984, 47(5):1130.
Huang et al., "A review of separation technologies in current and future biorefineries", Separation and Purification Technology, 2008, 62:1-21.
Hui et al., "Direct microbial conversion of wheat straw into lipid by a cellulolytic fungus of *Aspergillus oryzae* A-4 in solid-state fermentation", Bioresources Technology, 2010, 101:7556-7562.
Kocabas et al., "Optimization of xylanase production from *Aspergillus terreus* by using renewable agricultural lignocellulosic residues", New Biotechnology, Sep. 2009, 255:S145.
Lynd et al., "Consolidated bioprocessing of cellulosic biomass: An update", Current Opinion in Biotechnology, 2005, 16:577-583.
Marinova et al., "Addressing the increased energy demand of a Kraft mill biorefinery: The hemicellulose extraction case", Chemical Engineering Research and Design, 2009, 87:1269-1275.
Mendes et al., "Valorisation of hardwood hemicelluloses in the kraft pulping process by using an integrated biorefinery concept", Food and Bioproducts Processing, 2009, 87:197-207.
Peng et al., "Microbial oil accumulation and cellulase secretion of the endophytic fungi from oleaginous plants", Annals of Microbiology, 2007, 57(2):239-242.
Suutari et al., "Temperature adaptation in yeasts: the role of fatty acids", Journal of General Microbiology, 1990, 136:1469-1474.
Search Report for EP10196494 dated May 30, 2011.

* cited by examiner

INTEGRATED PROCESS SYSTEM FOR SINGLE CELL OIL PRODUCTION AND A PULP AND/OR PAPER INDUSTRY PROCESS

CROSS-REFERENCE TO RELATED APPLICATIONS

The present application claims the benefit of priority under 35 U.S.C. §119(e) to U.S. Provisional Application No. 61/459,964, filed on Dec. 22, 2010, the content of which is incorporated herein by reference in its entirety.

FIELD

The present invention relates to an integrated process system, wherein one of the processes is a pulp or paper industry process, and another process is a single cell oil production process (microbial lipid production process). The invention relates also to a process for producing lipids from pulp and/or paper industry residues in the integrated system and use of the lipids.

BACKGROUND

Hemicellulose represents a relative large fraction in wood materials, being typically from 20 to 40 weight % of the wood material depending on wood species. In chemical pulping processes, such as Kraft pulp and dissolving pulp processes, wood is delignified. In addition to lignin, hemicellulose is separated to a large extent from cellulose in the chemical pulping process, and the final pulp product contains only small amounts or no hemicellulose, depending on the process. Therefore, approximately half of the wood is dissolved in a chemical pulping process. In the pulping processes, such as Kraft pulping or sulphite pulping (dissolving pulp), the hemicellulose fraction that is separated from the pulp is mainly combusted and not valorized.

In the main pulping process, Kraft pulping (sulphate pulping or cooking), wood lignin and partly hemicellulose are dissolved in severe conditions in a digester (cooking). The hemicellulose degradation products in the resulting liquor (black liquor), are quite complex and their separation and purification from the liquor is difficult and its suitability for microbial processes is poor. For that reason the black liquor is combusted in the recovery boiler to produce electricity and thermal energy. However, hemicellulose has significantly lower heating value than lignin, the combustion of dissolved hemicelluloses does not constitute optimal economical use of this resource. Therefore, hemicellulose should preferably be extracted, prior to cooking, to produce higher value products. One option to valorize hemicellulose is to convert it into chemicals and/or to biofuels (e.g. ethanol, butanol) by microbiological processes. However, this hemicellulose pre-extraction before pulping should not decrease pulp yield or quality.

Dissolving pulp (also called dissolving cellulose) is a bleached wood pulp that has a high cellulose content (>90%). Dissolving pulp is a chemical pulp grade used as the raw material for a wide variety of cellulose derivatives, for example rayon (textiles), cellophane, cellulose acetate and methylcellulose. Dissolving pulp is made by the sulphite process or the kraft process with a step to extract the hemicelluloses before the pulping process. Hemicellulose is a byproduct which is largely being wasted at mills today as it is often combusted in the boilers and most of the energy is lost as waste heat.

Several different hemicellulose pre-extraction methods prior to Kraft-pulping can be applied, such as pressurized hot water extraction (hydrothermal treatment) and various organosolv methods using alcohols (e.g. ethanol, methanol) and/or organic acids (e.g. acetic acid, formic acid, malic acid, lactic acid or peracetic acid) possibly supplemented with acid catalyst such as $SO_2$. The methods can facilitate removal of mainly hemicellulose or both lignin and hemicellulose from pulp fraction. In majority of these pre-extraction methods, hemicellulose is obtained at least partly in oligomeric form. The oligomers need to be hydrolysed to monomers before they can be converted to end products by microorganisms. The conversion of sugar oligomers in hemicellulose to sugar monomers can be performed by specific enzymes, such as xylanases, arabinases, galactosidases and/or mannananes, depending on the type of hemicellulose (depending on the wood species). Such enzymes are produced by certain microorganisms, typically fungi or bacteria.

A biorefinery concept which includes pre-extraction of hemicellulose before pulping process and utilization of hemicellulose fraction to ethanol or chemicals production has been suggested in the prior art. A review of hemicellulose pre-extraction methods is presented in Huang et al. (2008) and an overview of Kraft-pulp biorefinery including hemicellulose pre-extraction by Marinova et al. (2009). Patent publication US20090165968 describes a method to pre-extract hemicellulose before Kraft-pulping process, which enhances the susceptibility of hemicellulose to biological fermentations for ethanol and chemicals. Production of ethanol from pre-extracted hemicellulose from eucalyptus Kraft-pulping process is described in Mendes et al. (2010).

Although in the prior art has been described various methods by which wood material and in particular hemicellulose can be extracted for pulp industry processes, there is still a need for new processes which would facilitate the fractionation and further valorization of wood material, in particular hemicellulose, for the pulp industry processes.

The degradation and utilization of lignocellulosic material is important also on other industrial fields than in pulp industry processes. Single-cell oils have traditionally been used as special products e.g. in health foods. Similar kind of production process has also been described for the production of lipids for biodiesel production. However, as the product is an inexpensive commodity chemical, the process costs should not be on the level of the process costs of special products. Further, the lipid yield by heterotrophic microorganisms is typically very low, less than 20% weight percent of the fed sugar, in the best case 22-24% from available sugars can be transformed to oil. Due to these reasons, the utilization of low-cost raw materials, such as lignocellulosic feedstock, for oil production is necessary.

A single cell oil production process using microorganisms generally comprises cultivating microorganisms in aerated bioreactors, allowing cells to accumulate lipids, harvesting lipid-rich cells and recovering oil from cells.

Utilization of cellulosic feedstock for oil production has been suggested in some recent patent publications. US 2009/0064567 A1 discloses the production of biological oils by heterotrophic fermentation by growing microorganism of the kingdom Stramenopile by using cellulose-containing feedstock as a main source of carbon. The cellulose is hydrolyzed by enzymes or by other microorganisms capable of saccharifying cellulose. WO2009/0011480 A1 discloses the production of biological oils from depolymerised cellulosic material by microalgae and fungi.

Patent publication US2009/217569 discloses single cell oil production from various lignocellulosic and other material hydrolysates, including wood and pulp and paper industry residues for manufacturing biofuel. The method comprises treating source material with water, acid or alkali and contacting filtrate or precipitate with lipid-producing microorganism. The prior art describes also lipid production directly from polymeric sugars in lignocellulose, such as xylan by Fall et al. (1984), or cellulose by Lin Hui et al. (2010) by organisms capable of producing cellulases or hemicellulases.

The enzymatic hydrolysis is typically performed in a separate step from biofuel production process by commercial enzymes. Typically commercial enzymes are bought, and produced outside the actual biofuel production process. The price of enzymes is the major cost factor in the conversion of cellulosic materials to biofuels by microbiological processes.

SUMMARY

It is one object of the present invention to provide a solution to problems encountered in the prior art. Specifically, the present invention aims to provide a technically beneficial solution to problems encountered in pulp and/or paper industry processes.

It is another object to provide a technically beneficial solution to problems encountered in the large-scale production of single-cell oil.

It is yet another object of the present invention to provide a solution, which enables upgrading the economy of large-scale single-cell oil production.

It is yet another object of the present invention to provide a solution, which enables reducing the environmental burden.

The present invention aims particularly to work out problems related to the manufacture of transportation biofuel.

To achieve these objects the invention is characterized by the features that are enlisted in the independent claims. Other claims represent the preferred embodiments of the invention.

The method according to the invention is based on the finding that the side streams of pulp and paper industry processes comprise a significant amount of nutrients, which can serve as carbon source for microorganisms, in particular for lipid producing microorganisms.

It has now been surprisingly found that the lipid production process produces a significant amount of proteins, in particular enzymes. More specifically, in connection with a single cell oil production process can be produced a significant amount of enzymes capable of degrading wood material or organic material from pulp and/or paper industry. In the present invention it has been found that enzymes produced in the lipid production process can be re-utilized in pulp and/or paper industry processes, such as in pulp industry processes, for example in pulp bleaching, pulp deinking, treatment of lignocellulose prior to chemical pulping, dissolving pulp making, debarking or fibre modification processes.

In one aspect the present invention provides an integrated system, which comprises a first process, which is a single cell oil production process, and a second process, which is a pulp and/or paper industry process. In the system organic material from pulp and/or paper industry is introduced into the lipid production process, and in the lipid production process is used a microorganism capable of producing lipids or lipids and enzymes when cultivated on a medium comprising organic material from pulp and/or paper industry. In an embodiment lipids or lipids and enzymes are produced by said microorganisms in the single cell oil production process. In another embodiment enzymes are produced in a process connected into the single cell oil production process.

The enzyme can be recovered from microorganism culture, spent culture medium or supernatant.

Typically the supernatant and microorganism cells are separated from the microorganism culture and lipids are recovered from the microorganism cells. In various embodiments of the invention the supernatant or a protein enriched fraction of the supernatant or a dilution of the supernatant comprising catalytically active enzymes are recovered from the lipid production process or from a process connected to it. In an embodiment the supernatant or a protein enriched fraction of the supernatant comprising enzymes are introduced from the lipid production process into the pulp and/or paper industry process.

In one embodiment of the invention the enzymes are produced in a process separate of the lipid production process or by another microorganism than the lipid producing microorganism.

In one preferred embodiment of the invention the enzymes and lipids are produced by the same microorganism.

In one preferred embodiment of the invention the microbiological lipid production process utilizes fractions or residues from pulp and/or paper industry, such as hemicellulose or primary sludges, such as from pulp or deinking processes, and it produces useful substances, such as enzymes, for use in pulp and/or paper industry processes. Simultaneously, the microbiological process produces substantial amounts of lipids that can be used for various purposes, e.g. production of biofuels. The integrated process system provides a way to more complete utilization and valorization of the lignocellulosic biomass in pulp and/or paper industry processes.

Pulp and/or paper industry can potentially produce larger variety of valuable side products by valorization of side streams than the prior art processes and enable competitive advantages.

In summary, it can be concluded that the invention offers benefits in that,

The invention described herein can improve cost-efficiency of pulp and/or paper industry processes.

Valorization of hemicellulose-stream by production of transportation biofuel results in economic benefits. In the prior art Kraft-pulp mills hemicellulose ends up in black liquor and is combusted.

The conversion of residues containing cellulose from pulp and/or paper industry, such as primary sludges from deinking, debarking, chemical pulp process, mechanical pulp process, or papermaking process. Production of valuable products such as lipids by microorganisms, adds value to the present process of aerobic and/or anaerobic waste water treatment.

Production of enzymes required in pulp and/or paper industry processes on site results in cost savings. It also reduces the need of enzyme stabilization prior to use.

Consolidated bioprocess for lipid production (enzymatic digestion and fermentation in the same process step) decreases cost and improves efficiency compared to processes featuring dedicated hemicellulose and/or production and lipid production stage. It reduces costs by eliminating or decreasing the need of buying enzymes outside.

Chemical pulping processes produce large amounts of surplus energy, mainly heat. Utilisation of excess heat from pulping process and results in improvement of energy efficiency. E.g., heat from pulping process (lignin combustion) to concentrate sugars in hemi-cellulose hydrolysate (syrup), to purifiy the hydrolysate, or in the recovery of solvents in the oil recovery in lipid production process.

The energy cost of treatment of lignocellulosic materials or materials comprising other polymeric carbohydrate biomass is reduced by using enzymes from the single-cell oil process itself in place of or in addition to commercial enzymes and thermo-mechanical and chemical treatments.

The removal of enzyme proteins from the remainder of the liquors from the single cell oil production fermentation reduces the biological oxygen consumption load of the fermentation liquor released from single cell oil production.

The carbon balance of a single cell oil process is improved when the enzyme proteins, instead of causing biological load in process streams, are reduced or removed from the fermentation waste water, reused for catalytic purposes or used as a nutrient in the single-cell oil production process or other biotechnical processes.

DETAILED DESCRIPTION OF THE INVENTION

Figure 1:
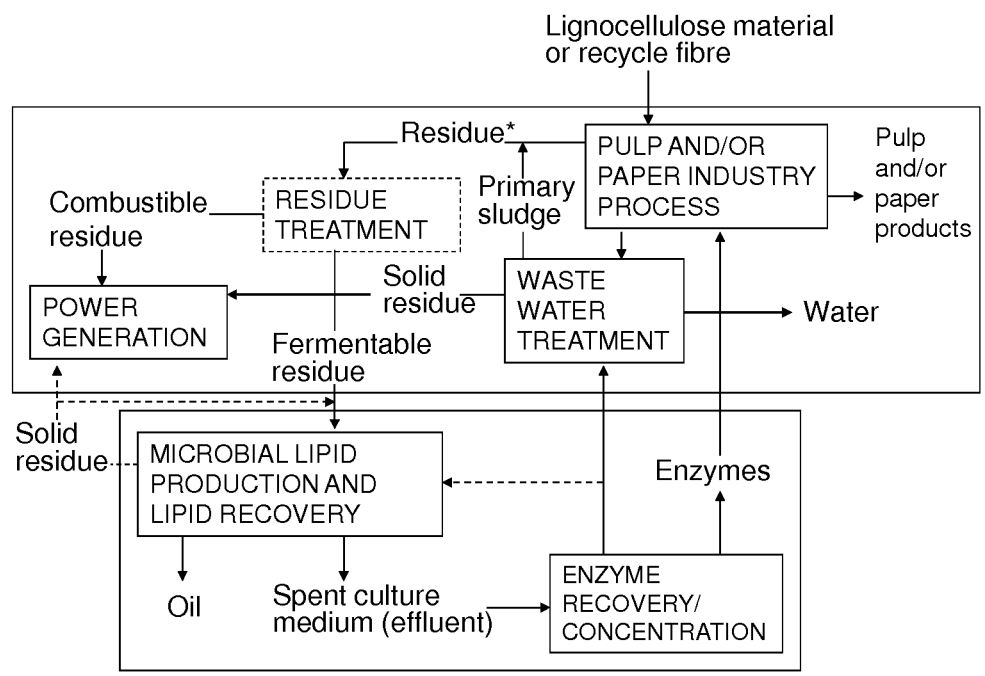
FIGS. 1 and 2 show process schemes.
Figure 2:
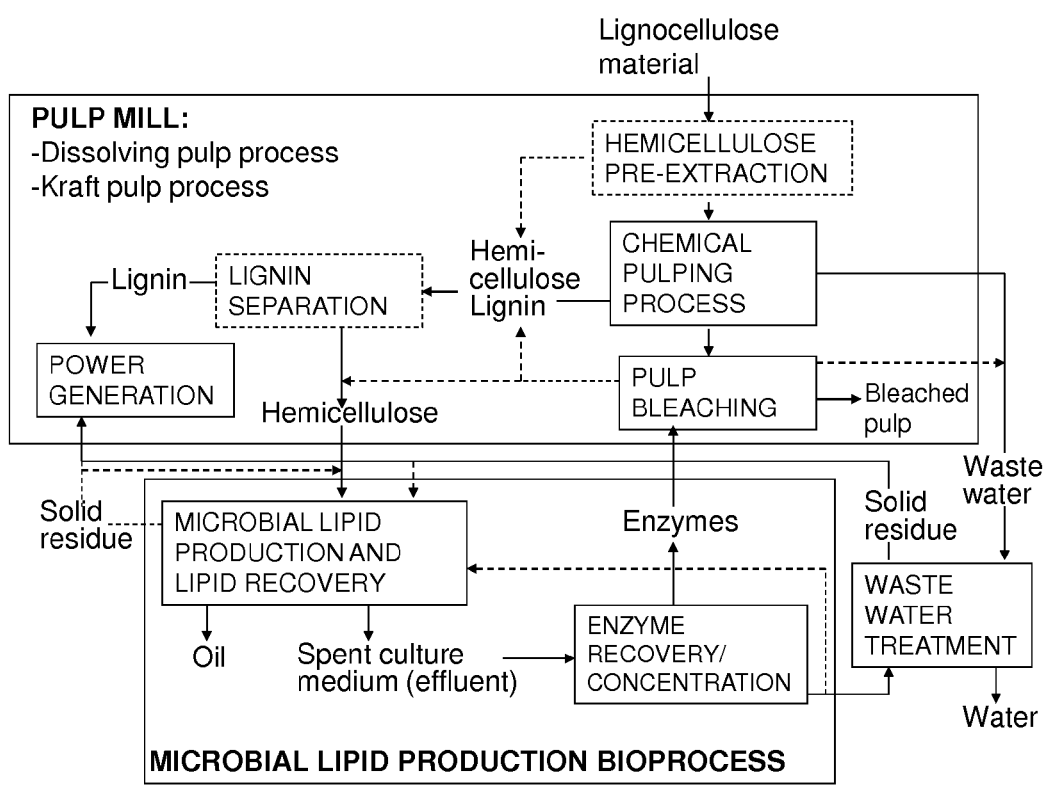

"A single cell oil production process" refers here to a process, comprising steps of forming or allowing the formation of a lipid synthesizing microorganism and allowing the thus obtained organism mass to produce and/or store (accumulate) lipid, recovering the cells from the liquid phase, and extracting or recovering the lipids from the cells and/or from the culture medium or liquid. As described here later in various microorganism groups, such as among bacteria, archaebacteria, fungi (filamentous fungi), yeast and algae, are single cell oil producing microorganisms, As described herein, the present invention uses preferably microorganisms capable of producing both lipids and enzymes. "A microorganism" refers in some embodiments of the invention to two or more microorganisms. In some embodiments, the enzymes are produced by one microorganism and the single cell oil (lipids) by another microorganism.

The term "single cell oil" refers to a fatty substance, whose molecule generally contains, as a part, an aliphatic hydrocarbon chain, which dissolves in nonpolar organic solvents but is poorly soluble in water. Single cell oils are an essential group of large molecules in living cells. Single cell oils are, for example, lipids, fats, waxes, wax esters, sterols, terpenoids, isoprenoids, carotenoids, polyhydroxyalkanoates, nucleic acids, fatty acids, fatty alcohols, fatty aldehydes, fatty acid esters, phospholipids, glycolipids, sphingolipids and acylglycerols, such as triacylglycerols, diacylglycerols, or monoacylglycerols.

Preferred single cell oils in the present invention are lipids, fats, waxes, acylglycerols and fatty acids and their derivatives, in particular triacylglycerols and wax esters.

In connection of this invention "lipid" is used as synonym for single cell oil and "lipid production process" as synonym for single cell oil production process.

"Pulp industry process" refers here to a process aiming for the production of pulp from lignocellulosic materials or recycled fibres as well as fibrous materials needed for pulp production.

"Pulp and/or paper industry" refers here to the branch of industry that produces various types of paper, paperboard, paper, newsprint, toilet paper and paperboard articles, pulp, and insulation boards and hardboards. Pulp and/or paper industry uses lignocellulosic materials or recycled fibres as raw materials. The pulp and/or paper industry includes processes such as chemical pulping, mechanical pulping, semi-chemical pulping, chemothermomechanical pulping, recycle fibre processes and papermaking.

"Chemical pulping" refers to a process, where lignocellulosic material such as wood or wood chips are treated with chemicals and heat which results in the removal of most of the lignin and thereby release of fibres without seriously damaging cellulose fibres. Typically, majority of the lignin and hemicellulose becomes water soluble in chemical pulping and is thus removed from the fibres in pulp. Approximately half of the wood material is dissolved in chemical pulping. The major methods for chemical pulping are Kraft pulping, and dissolved pulp process (sulphite process). Soda cooking is a modification to Kraft cooking process, in which sodium sulphite is not used.

"Kraft pulp process" or "Kraft pulping" or "Kraft cooking" refer to a chemical pulping process in which lignocellulosic material is treated with mixture of sodium hydroxide and sodium sulphide that break the bonds that link lignin to the cellulose. Soda cooking is a modification to Kraft cooking process, in which sodium sulphite is not used. Organic solvents, such as ethanol, methanol and peracetic acid can be used as a reinforcement chemical in Kraft pulp process.

"Dissolving pulp process" or "sulphite process" refer to a chemical pulping process in which sulphurous acid ($H_2SO_3$) and bisulphite ions act in the degradation and dissolving lignin. Acid sulphite pulping is performed at low pH, 1 to 2, while neutral sulphite pulping is performed at pHs 7 to 9. Organic solvents, such as ethanol, methanol and peracetic acid can be used as a reinforcement chemical in dissolving pulp process.

"Organosolv process" refers to a chemical pulping process with organic chemicals are used to achieve removal of lignin and release of fibres. Typical organic chemicals used in organosolv process include, but are not limited to methanol, ethanol, formic acid, acetic acid, peracetic acid, ethyl acetate and acetone. The removal of lignin in organosolv process may be reinforced by addition of with acid catalyst such as sulphuric acid or suphur dioxide ($SO_2$).

"Mechanical pulping" refers to a process in which the fibres in lignocellulosic material such as wood or wood chips are released mechanically such as by grinding. The main types of mechanical pulps include stone groundwood pulp and refiner pulp. Stone groundwood pulp is made by grinding of logs, and if wood if steamed prior to grinding it is known as pressure groundwood pulp. Refiner pulp is made by feeding wood chips to centre of rotating discs (refining), if the pulp is treated with steam prior to refining the pulp is called thermomechanical pulp. In making of chemo-thermomechanical pulp the wood is pre-treated with chemicals, such as sodium suphite, and steam to refining made by refining of chips. In all cases, the yield of pulp is high, typically 95 to 98%, meaning that all the wood components are retained in the fiber with only minor losses of easily water soluble substances, which differs from the chemical pulping processes where pulp yield is significantly lower.

"Recycle fibre process" or "Fibre recycle process" refers to process which uses used pulp products, such as paper, and remakes it into new pulp or paper products. The process enables the recycling and re-use of pulp and paper products. The recycle fibre process consists in general of three steps, repulping the paper, removal of contaminants, such as ink (deinking), and bleaching of fibres.

According to one preferred embodiment of the invention the hydrolysis and biofuel production are carried out utilizing microorganisms that are capable of both producing enzymes capable of hydrolysing oligomeric sugars and production of biofuels. Typically this is carried out in a single step.

According to a preferred embodiment of the invention, at least 5%, at least 10%, at least 20%, at least 30%, at least 40%, preferably at least 50%, more preferably at least 60%, more preferably at least 70%, more preferably at least 80%, still more preferably at least 90% of the certain enzymes, that are used in the pulp and/or paper industry process, are produced by a microorganism producing also lipids. In the pulp and/or paper industry process may be used several enzymes of which typically some enzymes or enzyme groups are produced in the integrated single cell oil production process or in a process connected to it and some enzymes or group of enzymes are obtained from other sources e.g. are for example commercial enzymes.

A microorganism producing lipids means here one or more lipid producing microorganisms, preferably one lipid producing microorganism.

According to another embodiment of the invention the enzymes are produced by one or more other microorganisms than the lipid producing microorganism in the same lipid production process or in a process connected to the process. The microorganism(s) may be (a) microorganism(s) producing efficiently specific enzymes, such as hydrolyzing enzymes, for example *Trichoderma* or *Bacillus*. "A process connected to the lipid production process" means for example a process, where the feedstock for the lipid production process is treated, e.g. with enzymes.

According to a further embodiment of the invention the enzymes are produced in a process separate from the lipid production process. The enzymes are produced for example in a separate process by a microorganism efficient in producing specific enzymes, such as hydrolytic enzymes. Alternatively, the enzymes are commercial enzymes.

According to further embodiment of the invention the hydrolysis and biofuel production are carried out in a similar way utilizing microorganisms that are capable of producing enzymes capable for hydrolysing oligomeric sugars and production of biofuels, but the produced enzymes are used separately to hydrolyse the raw material, such as cellulose (or hemicellulose) hydrolysis. The hydrolysis products are then used in the fermentation.

According to yet another embodiment of the invention heterotrophic microorganism-based lipid production process is integrated into a pulp and/or paper industry process. Heterotrophic microorganisms use residues or fractions from pulp and/or paper industry as raw materials for lipid production.

In an embodiment of the invention the organic material used for lipid production comprises at least 30%, preferably at least 50%, preferably 60% lignocelluloses, preferably at least 70%, more preferably at least 80%, still more preferably at least 90% lignocelluloses, or lignocellulose derived materials from pulp and/or paper industry.

In an embodiment of the invention the organic material from pulp and/or paper industry used in a lipid production process comprises at least 60% preferably at least 70%, more preferably at least 80%, still more preferably at least 90% of a fraction of lignocellulose, or materials derived from lignocellulose, such as hemicelluloses or cellulose.

In an embodiment of the invention the organic material from pulp and/or paper industry used in a lipid production process comprises at least 5%, at least 10%; at least 20%, preferably at least 30%, preferably at least 40, preferably at least 50%, preferably at least 60% preferably at least 70%, more preferably at least 80%, still more preferably at least 90% polymeric sugars.

The polymerization degree and the amount of monosaccharides in the hydrolysate from the delignification depend largely on the lignocellulose cooking or pretreatment method. Typically pressurized hot water extraction of lignocellulosic material results in hemicelluloe fraction that mainly consists of oligomeric hemicellulose. Dissolving pulp process, on the other hand, typically produces hydrolyse, i.e. spent sulphite liquer, where the hemicellulose sugars are mainly in the monomeric form.

In an embodiment of the invention the organic material from pulp and/or paper industry, potentially at least partial removal of lignin, used in a lipid production process comprises at least 20%, at least 30%, at least 40%, at least 50%, at least 60% preferably at least 70%, more at least 80%, still more preferably at least 90% hemicellulose or materials derived from hemicellulose.

In an embodiment of the invention the organic material from pulp and/or paper industry, at least partial removal of lignin, used in a lipid production process comprises at least 20%, at least 30%, at least 40%, at least 50%, at least 60% preferably at least 70%, more at least 80%, still more preferably at least 90% cellulose.

More specifically, suitable fractions for microbial lipid production include hemicellulose materials that are separated before actual pulping process. This integrate can be utilized in different types of pulping processes including Kraft pulp and dissolving pulp processes.

In an embodiment of the invention the cellulase and/or hemicellulase production, cellulose and/or hemicellulose hydrolysis and fermentation are carried out in one step. This offers the potential for lower cost and higher efficiency than processes featuring dedicated cellulase and/or hemicellulase production. This results in avoided costs of capital, substrate and other raw materials, and utilities associated with cellulase and/or hemicellulase production. In addition, it offers possibility to obtain higher hydrolysis rates, and hence reduced reactor volume and capital investment. The one step process reduces costs significantly by eliminating or at least diminishing the need for enzyme produced in a separate bioprocess.

In yet another embodiment of the invention, the heterotrophic microorganisms use primary sludge(s) from pulp and/or paper industry, such as deinking, debarking, chemical pulp, mechanical pulp or papermaking primary sludge(s). The primary sludges can be combined with other fractions or residues from pulp and/or paper industry, such as hemicellulose or cellulose.

The microorganisms used in lipid production are preferably such that are able to utilize polymeric hemicellulose by possessing exoenzymes, such as hemicellulases capable of hemicellulose degradation. The hemicellulases, such as xylanases, arabinases, mannanases, galactosidases, can be recovered from spent (used) culture medium from lipid production process and re-used in the pulping process, e.g. for pulp bleaching, pulp deinking, dissolving pulp making, or fiber modification. Such enzymes can be produced for example by fungi or bacteria, fungus preferably belonging to the genus *Aspergillus, A. oryzae, Humicola, Rhizopus,* or *Trichoderma,* or bacteria, preferably *Streptomyces.*

In another embodiment of the invention, lipid-producing microorganisms are used that are able to utilize polymeric sugars in hemicellulose and cellulose. The hemicellulases and/or cellulases can be recovered from the culture medium from lipid production process and re-used in the pulping process, e.g. in fiber modification, processing of recycled fibres or deinking. Such enzymes can be produced e.g. by fungi or bacteria, preferably belonging to the genus *Aspergillus*, such as *A. terreus,* or bacteria belonging to *Streptomyces.*

According to a preferred embodiment of the invention enzymes produced in lipid production from pulp and/or paper industry, such as from pulp and/or paper mill side streams or residues, such as hemicellulose stream or primary sludge, are recovered from microbiological process and utilized in pulp and/or paper industry, such as in pulp and/or paper mill. Preferably, the hemicellulase enzymes for a pulp (pre)bleaching application or for removal of residual xylan from dissolving pulp process possess low or no cellulose degradation activity, in order not to affect or degrade cellulose fibres in the pulp. Such enzymes can be produced e.g. by fungi, preferably belonging to the genus *Aspergillus*, such as *A. oryzae*, are also oleaginous and capable of accumulating lipids from hemicellulose. Alternative re-use application of hemicellulase enzymes is to recycle them back to the lipid production process.

Enzymes can be used in pulp and/or paper industry also to reduce paper manufacturing costs or to improve the product. Main uses of the enzymes include pulp bleaching, where hemicellulose enzymes (e.g. xylanases and mannanases) and possibly laccases are used in order to facilitate hemicellulose and/or lignin removal. Utilization of enzymes in pulp bleaching reduces the consumption of bleaching chemicals and results in both economic and environmental benefits. The enzymes used in pulping process are commercial enzymes produced in separate enzyme factories. The production of enzymes on-site could result in cost savings due to decreasing need for enzyme processing, such as stabilization before use.

Also many other applications for enzymes exist in pulp and/or paper industry, such as helping deinking, enhancing kraft pulping, decreasing vessel picking, facilitating retting, selectively removing fiber components, modifying fiber properties, increasing fiber flexibility, and covalently linking side chains or functional groups, debarking, cleaning paper machines and pitch and slime removal.

Pulp bleaching, i.e. removal of lignin from chemical pulps, is necessary for aesthetic reasons and for improvement of paper properties because the left-over residual lignin after sulphite pulping imparts an undesirable brown color to the paper. The aims of the enzymatic treatment depend on the actual mill conditions and may be related to environmental demands, reduction of chemical costs or maintenance or improvement of product quality.

The most important application of xylanase enzymes is in the prebleaching of kraft pulp, and xylanases have gained importance as alternatives to toxic chlorine-containing chemicals. Treatment of chemical pulps with xylanases leads to savings in the consumption of bleaching chemicals, decreased environmental loadings, and/or increases final brightness of pulp. The main driving force has been the economic and environmental advantages the enzyme brings to the bleach plant. Xylanases can be also used in the removal of shives, fibres that have not been separated into individual fibres in the pulping.

Xylanases can be used in processing of cellulosic pulps to remove the residual xylan in dissolving pulp process. Enzymes are able to degrade selectively the hemicellulose fraction without affecting the cellulose. Once hemicellulose is removed by hemicellulases, lignin is more easily removable and degradable by enzymes, such as laccase. The main enzyme needed to enhance the delignification of kraft pulp is endo-β-xylanase, but enrichment of other enzymes such as mannanase, lipase, and α-galactosidase has been shown to improve the effect of enzymatic treatment of kraft pulp. Xylanase enzyme can reduce the requirement for oxidizing chemicals by up to 20%-40%. (Beg et al. 2001). The resulting enzyme preparation must be completely free of any cellulase activity. In addition, xylanases that are active and stable at high temperature and alkaline pH are desirable (Beg et al. 2001). Alkalitolerant enzymes are preferred since they can function without pH adjustment in the pulp bleaching (Bajpai 2004).

Preferred microorganisms for producing xylanases, in particular for pulp bleaching are fungal xylanases of *Aspergillus* and *Trichoderma* species and bacterial xylanases of *Bacillus* species, *Streptomyces* species and *Clostridium* species. Of these genera, especially *Aspergillus* and *Streptomyces* contain oleaginous species, i.e. capable of accumulating substantial amounts of lipids (>15% of their cell dry weight) when cultivated in suitable or optimal conditions.

According to the invention, the microorganisms when cultivated on raw materials from pulp and/or paper industry, are able to produce and accumulate at least 3% (w/w) of lipids from their cell dry weight, preferably at least 5%, more preferably at least 10%, 15%, 20%, 30%, 40%, 50%, 60%

Enzymes can be also used in the fiber modification of pulps, especially pulp refining of mechanical pulping process. Enzymatic modification of fibers aims at decreased energy consumption in the production of thermomechanical pulps and increased beatability of chemical pulps or improvement of fiber properties.

Xylanase and pectinase enzymes can be used to aid debarking and can result in significant energy consumption in debarking process.

Mixture of xylanase and cellulase enzymes at low concentrations has been found to markedly increase the freeness of recycled fibers without substantially reducing yield.

Dissolving pulps can be used to produce cellulosic materials such as acetates, cellophanes, and rayons. Their manufacture is characterized by the derivatization and thus solubilization of highly purified cellulose. The removal of hemicellulose from pulps requires the use of high caustic loadings and appropriate pulping conditions, such as sulfite pulping and acid-pretreated kraft pulping. Xylanase treatment in dissolving pulp process may reduce the chemical loading required during the caustic extraction or facilitate hemicellulose extraction from kraft pulps.

Enzymes can be used in the pulp deinking to convert secondary fibres into high quality products. Enzymes utilized in the deinking can be for example cellulases, hemicellulases, laccases, esterases, lipases and pectinases.

Lipases can be used in the removal of pitch in pulping which causes operation problems in paper machines. Specific enzymes, such as levan hydrolases, amylases and proteases have can also be used to clean and reduce slime in paper machines.

Hemicellulose represents a relative large fraction in wood materials, being typically from 20 to 40 weight-% of the wood material depending on wood species. Hemicellulose is separated from cellulose in the pulping process, and the final pulp product contains only small amounts or no hemicellulose depending on the process. In order to integrate lipid production process with a traditional Kraft-pulp process, additional hemicellulose separation unit process is required before the actual pulping process. Such unit process can be any process that separates hemicellulose from lignocellulosic material, such as, but not limited to pressurized hot water extraction (hydrothermal treatment), acid treatments or organosolv treatments.

In the case of dissolving pulp process, the prior art processes, such as dissolving pulp process or kraft-process with hemicellulose extraction (such as acid treatment), the processes produce hemicellulose and lignin stream, which contain fermentable sugars, and lipid production process can be more readily integrated to pulping process.

The extraction or separation method for hemicellulose from lignocellulose prior to pulping can be done by any known method. Preferably, the separation of hemicellulose is performed with a method that produces, after possible purification and concentration, hydrolysates which do not inhibit the growth of lipid producing microorganisms. Preferably, the method provides hemicellulose fraction, which contains at least part of the sugars in oligomeric form. One embodiment of the invention is to use pressurized hot water extraction to extract hemicellulose. In addition to hemicellulose, pressurized hot water extraction removes minerals from lignocellulosic materials that can be preferable in fermentation and reduce the need of mineral additions in culture medium.

In certain pre-treatment applications, such as in some organosolv treatments or in spent sulphite liqueur, significant amounts of both hemicellulose and lignin can be solubilised from the pulp fraction which remains solid. In these cases, the separation of hemicellulose sugars and lignin is preferred before aerobic microbiological lipid production process. The separation of lignin fraction from hemicellulose sugars can be performed with any known method. In organosolv treatments lignin removal is promoted by direct action of an organic solvent (ethanol, methanol, acetone, acetic acid, formic acid, ethyl acetate, etc.) to solubilize lignin and hydrolyze hemicellulosic fraction. A general method to separate lignin from hemicellulose hydrolysate is to add water which results in precipitation of lignin.

The hemicellulose hydrolysate may need to be treated with different unit operations before feeding to microorganisms. Separation of lignin of residues of lignin may be required. Sugars in hemicellulose hydrolysate may need to be concentrated e.g. by evaporation of water. Further, it may be required to get rid of organic compounds such as acids (organic acids) released in the pre-treatment, or solvents such as alcohols or acids, or other compounds such as $SO_2$, used in the hydrolysis. Methods, such as but not limited to stream stripping, evaporation or distillation may be used. These processes of evaporation, distillation or stripping can utilize process heat and stream from pulping process (combustion of lignin). The utilization of process heat is advantageous, since typically pulp mills produce excess heat that cannot be utilized. In addition, the sugars may need to be concentrated by filtration or membrane technologies or application. For example, oligomeric sugars in hemicellulose may be concentrated by membrane filtration. The hemicellulose hydrolysate may need to be further purified before feeding to microorganisms. Hydrolysate conditioning methods to remove inhibitory compounds may contain, but are not limited to precipitation, filtration, stripping or adsorption, or enzyme treatment.

The invention described can be applied to pulping processes using any materials or mixes thereof including but not limited to softwood (such as pine, spruce), hardwood (such as eucalyptus, birch, aspen, poplar, oak), bamboo, rice straw, barley straw, wheat straw, corn stalk, oil palm empty fruit bunches and bagasse. Preferably the hemicellulose fraction from lignocellulosic material is used as a raw material for lipid production. The invention is not limited to the utilization of hemicellulose stream, or any fractions thereof, as raw material for lipid production, also streams containing cellulose, of any fractions thereof, and/or other compounds suitable for lipid production can be used. The lipid production process can also utilize other streams from pulp and/or paper industry, such as waste fibre or primary sludge from pulp and/or paper industry. For example, the hemicellulose feed can be supplemented with other streams from pulp and/or paper industry. In addition, the lipid production process can be supplemented with other raw materials than those from pulp and/or paper industry, such as lignocellulosic materials like agricultural residues, energy crops, paper waste, algae biomass, residues from food industry, municipal solid organic waste, biowaste from institutional kitchens, starch (such as corn starch, wheat starch, potato starch, cassava starch etc.) or sugars, such as molasses from sugar cane or sugar beet. The raw material for lipid production can also include raw materials of additives, such as starch or residues thereof, which are used in a paper making process.

According to a preferred embodiment of the invention the hemicellulose stream from pulping process, or separated prior to pulping process, is utilized for lipid production by microorganisms. Also fermentable fraction of hemicellulose produced in pulping process is within to the scope of the invention. For lipid production, microorganisms capable of utilizing sugars derived from hemicellulose are utilized. The microorganisms can be any organisms that are capable of accumulating and/or producing lipids (oleaginous microorganisms). Such microorganisms are bacteria, yeasts, filamentous fungi (moulds) or algae that can grow heterotrophically or mixotrophically.

The microorganism may be able to utilize other compounds than sugars included in the hemicellulose hydrolysate, such as organic acids derived from lignocellulosic biomass for growth and lipid production. The microorganisms may also utilize compounds, such as organic acids or alcohols, added as reagents in the hemicellulose extraction for growth and lipid production. Low amounts of these compounds, typically 0.01 to 10%, may remain in hydrolysate after removal of majority of these reagents. The presence of these compounds can be advantageous to the microbiological process of lipid production.

The sugars in hemicellulose can be in monomeric and/or in oligomeric form for lipid production. In one, most preferred embodiment of the invention, sugars are mainly in oligomeric form. Typically, at least 5, at least 10%, at least 20%, preferably at least 30%, preferably at least 40%, preferably at least 50%, preferably at least 60%, preferably at least 70%, preferably at least 80%, more preferably at least 90% of the amount of sugars is in oligomeric and/or polymeric form.

In one, most preferred embodiment of the invention, the lipid production process utilizes microorganisms, which are able to utilize polymeric sugars by exoenzymes, such as hemicellulases, xylanases, arabinases, mannanases or galactosidases. Microorganisms used in the invention possess enzymes or are capable of producing, which are able to degrade and utilize oligomeric hemicellulose sugars from different materials such as wood materials including galactoglucomannans in hardwood and xylan in softwood, and (arabino)xylans in herbaceous materials, such as straw. The polymeric sugar degrading exoenzymes produced by microorganisms can be concentrated or recovered from spent culture medium and reused in the pulping process as dilution or as process water. Hemicellulases are widely used in pulping processes, e.g. in pulp bleaching and fiber modification. For pulp bleaching purpose, it is preferred that the hemicellulases are thermostable and tolerate alkaline pH. This will decrease the need of cooling and pH adjustment of pulp stream before enzymatic treatment, which can simplify the process and result in savings in capital and operational costs.

Pulp and/or paper industry produces a various waste or residue streams containing polymeric sugars such as cellulose and/or hemicellulose, depending on the process. The main waste water treatment process used at pulp and paper mill plants is primary sedimentation (clarification, settling) where solid matter is removed. This is considered a primary treatment of the waste water and the solids produced are known as primary sludge. The primary sludges typically contain oligomeric cellulose, hemicellulose and lignin and/or inorganic compounds. The primary sludge is a suitable raw material for lipid production by microorganisms. According to the invention, primary sludge(s) from pulp and/or paper industry are used for lipid production by microorganisms. The primary sludges may be pretreated to improve the biodegradability of sugars, or treated to reduce the amount of lignin or residues of lignin, inorganic compounds, or inhibitory compounds before feeding to bioprocess.

In preferred embodiment of the invention such microorganisms are used that are capable of producing lipids and enzymes capable of hydrolysing polymeric sugars. Such enzymes enriched and/or recovered from used culture medium and be reused in pulp and paper industry process.

The primary sludges from pulp and/or paper industry include, such as deinking, debarking, chemical pulping, mechanical or semi-chemical pulping and papermaking primary sludges. Chemical pulping primary sludge include, Kraft-pulp process primary sludge and dissolving pulp process primary sludges. Mechanical pulp primary and semi-chemical pulping primary sludges include those from stone groundwood (SGW), pressure groundwood (PGW), refiner mechanical pulp (RMP), and thermomechanical pulp (TMP) processes. Deinking process primary sludge comes from paper mill using recycled fibre, the sludge can contain dye, colorant, glue, cohesion agent as well as paper fillers and other inorganic additives in addition to cellulose fibre. The sludge requires typically at least partial separation of inorganic constituents from fibre before feeding to microbial lipid production process. The primary sludge from paper mills contain papermaking fillers such as clay, calcium carbonate, talc, and titanium dioxide in addition to cellulose fibres. Typically, at least partial separation of these inorganic compounds is required feeding to microbial lipid production process.

In one embodiment of the invention, microbial lipid production process is integrated to a recycle fibre process (recycle pulp process). Primary sludge from pulp and paper industry process, such as deinking sludge is used as raw material for lipid production by microorganisms. Deinking sludge may be treated to reduce content of inorganic compounds or organic or inorganic inhibitory compounds before feeding to bioprocess. Deinking sludge can be supplemented with other raw materials from pulp and/or paper industry or from elsewhere, such as agricultural lignocellulosic residues, energy crops, microalgae, sugar crops, starch, sucrose or molasses. The microbiological process using at least some primary sludge or other organic residues from recycle fibre process, such as deinking, produces lipids that can be recovered and converted to biofuels, and enzymes that are, e.g. capable of hydrolysing polymeric sugars. The enzymes can be recovered and/or enriched from the spent culture medium and re-used in a pulp and/or paper industry process, such as in recycle fibre process, in paper deinking. The enzymes recovered can be also used elsewhere in pulp and paper industry process or sold and used in any other processes.

The enzymes in the spent culture medium, capable of hydrolysing polymeric sugars, include for example cellulases and/or hemicellulases depending on the microorganism used. Preferably, both cellulases and hemicellulases are included in spent culture medium. Lipid production process from primary sludge can be supplemented with other residues from pulp and/or paper industry processes, or from raw materials from elsewhere, such as agricultural residues, food industry residues or lignocellulosic biomass or starch or molasses.

The exoenzymes produced on site by feeding microorganisms hemicellulose that has been extracted from the same material that is used for pulp production. Therefore, the exoenzymes produced on site are very suitable for pulp bleaching on the site.

In one embodiment of the invention, a supernatant resulting from the treatment of pulp or pulp and/or paper industry stream with enzymes in a pulp and/or paper industry process is recycled back to the microbial lipid production process. The supernatant can contain compounds that are advantageous for growth and lipid production of lipid producing microorganisms. For example, the supertant can contain sugars suitable for microbial growth and lipid production, minerals for microbial growth and/or enzymes that hydrolyse polymeric sugars. In one embodiment of the invention, the supernatant resulting from the enzymatic pre-bleaching of pulp, such as treatment with hemicellulases, is recycled back to the microbial lipid production process. In another embodiment, the supernatant from enzymatic treatment of dissolving pulp for the removal of hemicellulose in pulp is recycled to lipid production process. The supernatant may be concentrated, and/or protein fraction collected, before feeding to microbial lipid production process.

According to one embodiment of the invention also microorganisms that are not able to utilize sugar oligomers or polymers for lipid production can be used and are within the scope of the invention. In this case, the raw materials from pulp and/or paper industry, such as from hemicellulose, primary sludge or waste fibre, are fed as sugar monomers to lipid production process. Hydrolysis of hemicellulose polymers to monomers can occur due to hemicellulose extraction procedure or due to addition of enzymes capable of hydrolysing sugar polymers. The enzymatic hydrolysis of hemicellulose and/or cellulose in raw materials can be performed in a separate process stage from oil accumulation, or simultaneously during oil accumulation, according to so called simultaneous saccharification and fermentation approach.

Furthermore, within the scope of the invention is an embodiment, where different organisms (two or more) are used for the hydrolysis of polymeric sugars and production of lipids from sugar monomers. Such a process is characterized in that the process comprises a first microorganism, for example a filamentous fungus, yeast or bacterium strain, which is capable of hydrolysing (depolymerising) polymeric organic compounds—such as hemicellulose or cellulose and a second microorganism, such as a yeast, bacterium, algae or filamentous fungus strain, which is capable of using the resulting hydrolysis products for its growth and single-cell fat production. Such processes steps can be implemented either as sequential processes or concurrently. A microorganism strain capable of hydrolysing polymeric organic compounds can be replaced by using enzymes with a capability of hydrolysing such compounds. The enzyme treatment can be conducted prior to or concurrently with the microbial production of single-cell fat. The operation of bioprocess with two or more species can be performed by any methods, including, but not limited to operation in same bioreactor at the same time as co-cultures, or separating process phases of hemicellulose hydrolysis and lipid production in time or space. In any of the cases, according to the invention, the enzymes involved in the hydrolysis of sugar polymers can be recovered from the culture medium and re-used in the pulping process.

The lipid production process can be also integrated with mechanical pulping process. The lipid production can use residues, such as water soluble substances created in pulping, as raw materials. The water soluble residues in general contain hemicellulose components, such as acetylated galactoglucomannan. The lipid production process can be supplemented with other residues from pulp and/or paper industry processes, or from elsewhere, such as agricultural residues, food industry residues or lignocellulosic biomass or starch or molasses. The enzymes produced in lipid production can be re-used in mechanical pulping, e.g. but not limited to pre-treatment of wood chips, or fibre modifications or bleaching. The enzymes produced in lipid production using residues from mechanical pulping process can be also recovered and re-utilized in other pulping processes such as chemical pulping or in treatment of the products from chemical pulping process.

Some oleaginous microorganisms are capable of utilizing sugar monomers in hemicellulose, such as xylose in xylan or xylan and arabinose in arabinoxylan or mannose, galactose or glucose in galactooglucomannan. Lipid producing organisms can utilize one or several of the above mentioned compounds. Lipid producing organisms are selected from the group of bacteria, cyanobacteria, fungi such as yeasts and moulds (filamentous fungi), archaea, or microalgae. The microorganisms can readily accumulate lipids or have been genetically modified to accumulate lipids or to improve accumulation of lipids. Lipid producing organisms include, but are not limited to the, following organisms:

Microalgal species belonging to the genera comprising *Dunaliella, Chlorella, Botryococcus, Brachiomonas, Chlorococcum, Crypthecodinium, Euglena, Haematococcus, Chlamydomas, Isochrysis, Pleurochrysis, Pavlova, Prototheca, Phaeodactylum, Pseudochlorella, Parachlorella, Bracteococcus, Scenedesmus, Skeletonema, Chaetoceros, Nitzschia, Nannochloropsis, Navicula, Nannochloris, Scihizochytrium, Sceletonema, Thraustochytrium, Ulkenia, Tetraselmis* and *Synechocystis*.

Filamentous fungal species belonging to the following genera *Aspergillus, Mortierella, Chaetomium, Claviceps, Cladosporidium, Cunninghamella, Emericella, Fusarium, Glomus, Mucor, Paecilomyces, Penicillium, Pythium, Rhizopus, Trichoderma, Zygorhynchus, Humicola, Cladosporium, Malbranchea, Ustilago*.

Yeasts belonging to the following genera *Clavispora, Deparyomyces, Pachysolen, Kluyveromyces, Galactomyces, Hansenula, Saccharomyces, Waltomyces, Endomycopsis, Cryptococcus*, such as *Cryptococcus curvatus, Rhodosporidium*, such as *Rohodosporidium toruloides, Rhodotorula*, such as *Rhodotorula glutinis, Yarrowia*, such as *Yarrowia lipolytica, Pichia*, such as *Pichia stipitis, Candida* such as *Candida curvata, Lipomyces* such as *Lipomyces starkeyi* and *Trichosporon* such as *Trichosporon cutaneum* or *Trichosporon pullulans*.

Bacteria belonging to the following genera *Acinetobacter, Actinobacter, Alcanivorax, Aerogenes, Anabaena, Arthrobacter, Bacillus, Clostridium, Dietzia, Gordonia, Escherichia, Flexibacterium, Micrococcus, Mycobacterium, Nocardia, Nostoc, Oscillatoria, Pseudomonas, Rhodococcus, Rhodomicrobium, Rhodopseudomonas, Shewanella, Shigella, Streptomyces* and *Vibrio*. Most preferably bacteria comprise *Rhodococcus opacus, Acinetobacter, Nocardia* or *Streptomyces*.

In preferred embodiments of the invention oleaginous, lipid producing organisms that are capable of utilizing polymeric hemicellulose or cellulose due to exoenzymes (such as hemicellulases, for example xylanases, galactosidases or mannanases, or cellulases) are used. These organisms include but are not limited to bacteria, such as *Streptomyces* or *Bacillus*, filamentous fungi, such as *Aspergillus, Fusarium, Humicola, Penicillium, Phanerochaete, Rhizopus*, or *Trichoderma*, such as *A. niger, A. terreus, A. oryzae, A. nidulans, F. oxysporum, Phanerochaete chrysosporium, Rhizopus oryzae* or *Trichoderma reesei*, yeasts such as *Cryptococcus* or *Trichosporon*, such as *Cryptococcus albidus, Trichosproron cutaneum*. Oleaginous microorganisms that are genetically modified to be able to utilize polymeric sugars in hemicellulose or cellulose are also part of the invention. Further, organisms capable of utilizing polymeric sugars in hemicellulose or cellulose that are genetically modified to improved production of lipids are also included in this invention.

In the most preferred embodiments of the invention, lipid producing organisms are used which are able to utilize polymeric sugars in lignocellulose, especially hemicellulose. Such organisms are preferably those from the following genera of filamentous fungi *Aspergillus, Humicola, Rhizopus, Trichoderma*, yeasts *Cryptococcus* or bacteria *Streptomyces*.

Other Enzymes than Hemicellulases

Hemicellulases are the main enzymes applied in the pulp and/or paper industry. Also the recovery and utilization of other enzymes than hemicellulases from the lipid production process in pulp and/or paper industry process are encompassed by the invention. Such enzymes may include, but are not limited to cellulases, laccases, pectinases, lipases, amylases, esterases and proteases.

Another feature of the invention is to utilize at least a part of the lignin of fractions thereof produced or liberated in the pulping or pre-extraction of hemicellulose, (per)bleaching, primary sludges, or included in other pulp and/or paper industry residues is used to produce enzymes that are capable for the degradation, modification or structural changes of lignin. Such enzymes can be used in several applications, such as, but not limited to, pulp (pre-)bleaching, pulp deinking, treatment of lignocellulose prior to chemical pulping, dissolving pulp making, debarking, or fibre modification.

Another feature of the invention is to utilize at least a part of the cellulose fraction (pulp) to produce enzymes capable of degrading cellulose. Such enzymes can be used e.g. in the fiber modification or pulp deinking. The production of cellulases can be performed by using oleaginous microorganisms capable of utilizing cellulose by possessing cellulase activity. Therefore, production of lipids and cellulases can be combined alike the production of lipids and hemicellulases.

Yet another feature of the invention is to produce pectinases from pulp and paper industry streams. The production of pectinases can be combined with lipid production. Pectinases can be used e.g. in fibre modification, pulp deinking, debarking or retting of flex fibres.

The production of exoenzymes by production organisms decreases the need for buying enzymes outside, which improves the cost-efficiency of the whole process. The utilization of enzymes at the same site decreases the costs attributed to the purification and stabilization of enzymes. Alternatively, the enzymes can be recovered, purified and stabilized and sold out as a high value by-product.

Lipid Production Process

Microbial lipid production can be performed with any known method or a method developed in the future. Typically the microbial lipid production process includes cultivation of microorganisms in aerated bioreactors in submerged cultivation. Microorganisms are grown in a liquid culture medium comprising carbon and energy sources, such as hemicellulose sugars, and macro- and micronutrients. Cultivation can be performed e.g. as batch cultivation, fed-batch cultivation, continuous cultivation. Cultivation can be also performed in a cascade process. In cultivation, microorganisms are let to grow and accumulate lipids intracellularly. Some microorganisms can also be able to excrete the lipids to culture medium.

The microbial lipid production process can be carried out also in reactors, where the amount of free water is low or where the production is carried out on a solid or semisolid surface. The cell mass or other biomass not dissolving in water, can be extracted with aqueous solutions in order to obtain enzymes into soluble form.

In various embodiments of the invention, oil, or precursors for oil, may be recovered from cell biomass or culture broth using any method known in the art or developed in the future. For example, microorganisms may be separated from the medium using a filtration or decanting techniques. Alternatively, centrifugation with industrial scale commercial centrifuges of large volume capacity may be used to separate the desired products.

In various embodiments of the invention, bacterial cells may be disrupted to facilitate the separation of oil and other components. Any method known for cell disruption may be used, such as ultrasonication, osmotic shock, mechanical shear force, cold press, thermal shock, enzyme-catalyzed or self-directed autolysis. Oil can be recovered from cells by extraction with organic solvents or by any method known in the art or developed in the future.

Other Products than Lipids

Also the microbiological production of other compounds than lipids from hemicellulose and/or cellulose from raw materials or residues from pulping process following the recovery and/or re-utilization of enzymes in the pulping process is part of the invention. Such products include microbiological production of alcohols, ethanol, butanol, acetone-ethanol-butanol (ABE), iso-butanol, 2,3 propanediol, lactic acid and succinic acid.

Purpose for the lipids or a fraction of the lipids produced with the method described is not restricted to any certain application. The lipids can be used, e.g. but not limited to, in food or feed purposes, in cooking, as nutraceuticals, in production of soap or detergents, in production of cosmetics as chemicals or raw material for production of chemicals, as biofuel or as raw material for the production of biofuel or as lubricants as base oils for lubricants (lubrication oils) or as a starting material for production of base oils for lubricants.

Preferably, the lipids recovered from microbial biomass with the method described in this invention can be used as feedstock for the production of biodiesel, renewable diesel, jet fuel or gasoline. Biodiesel comprises fatty acid methyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogen deoxygenation, hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications.

"Biofuel" refers to solid, liquid or gaseous fuel mainly derived from biomass or biowaste and is different from fossil fuels, which are derived from the organic remains of prehistoric microorganisms, plants and animals.

According to EU directive 2003/30/EU "biodiesel" refers to a methyl-ester produced from vegetable oil or animal oil, of diesel quality to be used as biofuel. More broadly, biodiesel refers to long-chain alkyl esters, such as methyl, ethyl or propylesters, from vegetable oil or animal oil of diesel quality. Biodiesel can also be produced from microorganism lipids, whereby microorganism lipid can originate from a bacterium, a fungus (a yeast or a mold), an algae or another microorganism.

"Renewable diesel" refers to a fuel which is produced by a hydrogen treatment of lipids of an animal, vegetable or microorganism origin, or their mixtures, whereby microorganism lipid can originate from a bacterium, a fungus (a yeast or a mold), an algae or another microorganism. Renewable diesel can be produced also from waxes derived from biomass by gasification and Fischer-Tropsch synthesis. Optionally, in addition to hydrogen treatment, isomerization or other processing steps can be performed. Renewable diesel process can also be used to produce jet fuel and/or gasoline. The production of renewable diesel has been described in patent publications EP 1396531, EP1398364, EP 1741767 and EP1741768.

Biodiesel or renewable diesel may be blended with mineral oil based diesel. Suitable additives, such as preservatives and antioxidants may be added to the fuel product.

"Lubricant" refers to a substance, such as grease, lipid or oil, that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demulsifiers, antifoaming agents, cosolvents, and lubricity additives (see for example U.S. Pat. No. 7,691, 792). Base oil for lubricant can originate from mineral oil, vegetable oil, animal oil or from a bacterium, fungi (a yeast or a mold), an algae or another microorganism. Base oil can also originate from waxes derived from biomass by gasification and Fischer-Tropsch synthesis. Viscosity index is used to characterise base oil. Typically high viscosity index is preferred.

The term "lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty acid esters, phospholipids, glycolipids, sphingolipids and acylglycerols.

The term "acylglycerol" refers to an ester of glycerol and fatty acids. Acylglycerols occur naturally as fats and fatty oils. Examples of acylglycerols include triacyiglycerols (TAGs, triglycerides), diacylglycerols (diglycerides) and monoacylglycerols (monoglycerides).

"Spent cultivation medium" or "spent culture medium" refers to a medium used in the cultivation of microorganisms and comprising the products accumulated by the microorganisms. More broadly the spent cultivation medium can be defined as a fraction of cultivation medium taken from a microbial cultivation during or after cultivation. The spent cultivation medium can be called also as spent cultivation broth.

The oil extracted cell residue can be used for energy production, e.g. combusted or treated with anaerobic digestion process, or utilized as animal feed. Oil-extracted cell residue, or a fraction of the cell residue, can also be recycled back to the cultivation process to be used as a source of nutrients.

The invention described here can be applied to any pulping processes including, but not limited to Kraft process, dissolving pulp process or organosolv process. In the case of dissolving pulp process, the present process, such as sulfite process or kraft-process with hemicellulose extraction (such as acid treatment), can already include hemicellulose separation before pulping, and lipid production process can be more readily integrated to pulping process.

The production of enzymes for pulp and/or paper process on-site is advantageous for several reasons and can improve the cost-efficiency of the pulping process.
  reduced down-stream processing costs including water and enzyme stabilization,
  decreased transportation and packaging costs,
  decreased losses via direct transfer of enzymes to pulping process,
  decreased capital costs vs. dedicated (remote) facilities,
  the utilization of same raw material or raw material from same source for enzyme production and pulp/paper process results in direct induction and adaptation of enzymes to the raw material
  straight forward process control and output tuning and improvement opportunities directly within the biorefinery in enzyme production and pulp/paper process.

Recovery of Enzymes from Spent Culture Medium

The enzymes can be recovered from microorganism culture, spent culture medium, supernatant by any known and suitable method or by any suitable method developed in the future. The same applies also to methods by which the enzymes can be separated into fractions with the desired enzyme activities.

The concentration, separation or recovery of enzymes from spent culture medium can be made by any known method or a method developed in the future. The recovery is performed with a method that preserves activity of the desired enzyme(s). Enzymes in spent culture medium may be also re-used without any concentration, separation or recovery of enzymes.

A method by which the microorganism culture or the supernatant or the enriched protein fraction comprising catalytically active enzyme(s) are recovered can be based on their molecular size, ionic behavior, solubility in water, solubility in different solutes or solubility in mixture solutes containing a buffering factor or a surface active factor or a surface-active compound or a salt.

The enzymes can be recovered from the culture medium by various procedures, including but not limited to procedures such as centrifugation, filtration, extraction, spray-drying, evaporation, or precipitation.

If needed the enzymes may be purified or isolated by various procedures including but not limited to chromatography, electrophoretic procedures, differential solubility, SDS-PAGE, or extraction.

The enzymes may be stabilized for example by salt, sugar or glycerol.

Furthermore, the enzymes may be formulated for the desired application.

By "conditions suitable for lipid production" are meant any conditions under which the microorganism is able to grow and produce lipids.

By "conditions suitable for enzyme production" are meant any conditions under which the microorganism is able to produce enzymes.

As described herein, a microorganism capable of using extracellular polymeric or oligometric compounds as their nutrition, carbon and/or energy sources, are cultivated on a cultivation medium comprising polymeric biomass containing these compounds. The microorganism is allowed to produce lipids.

"A cultivation medium" refers here to a medium used for cultivating microorganisms. The cultivation medium comprises here typically at least partly raw material from pulp and/or paper industry containing at least partly polymeric or oligometric compounds, such as polymeric sugars. The cultivation medium may be supplemented with minerals, micronutrients, macronutrients and buffering agents.

A preferred feedstock in the embodiments of the invention is polymeric biomass comprising lignocellulose, cellulose, hemicellulose and/or lignin, or other components of lignocellulose, as such or as a combination, or biomass treated chemically or physically or by their combination in order to improve the access of hydrolytic enzymes to sucar polymers. The lignocellulose feedstock is preferably a residue from pulp and paper industry, containing at least some polymeric sugars of hemicellulose and/or cellulose. Such as residue from pulp and/or paper industry, include, but are not limited to hemicellulose from chemical pulping process, primary sludge from chemical pulping, mechanical pulping, deinking or papermaking process or waste fibre.

The pretreated biomass is typically a biomass comprising hexose and/or pentose sugars. The biomasses may be treated prior to or after enzyme treatment by chemical, physical (such as (thermo)mechanical), biological means or by any combinations thereof and used thereafter for single-cell oil production.

"Polymeric sugar" refers to natural organic material or organic material treated by different chemical or physical methods or by their combination. Polymeric sugar means here typically an industrial product or a side stream of a pulp and/or paper industry process, such as a fraction containing hemicellulose or cellulose.

"Separating the supernatant and microorganism cells from the cultivation medium" means any process by which a separate cell fraction and a supernatant fraction are obtained.

By "enzyme" is in the present invention meant in particular an extracellular enzyme capable of degrading complex carbohydrates and proteins. More specifically the enzyme is a hydrolytic enzyme degrading a glycosidic bond or a peptide, ester or ether bond or a bond between nitrogen and carbon or nitrogen and oxygen. The enzyme is preferably a cellulase, xylanase, mannanase, galactase, pectinase, lipase, protease or esterase.

The enzyme preparation obtained as described herein is the microorganism culture or preferably the supernatant or the enriched protein fraction comprising catalytically active enzyme. Typically the enzyme preparation is the process water of a single cell oil production process, or a process water, where the protein fraction is enriched. The enrichment can be carried out by any suitable method used for enriching or concentrating proteins in biologically active form.

"Enriching a protein fraction" refers here to any method enriching the proteins in the supernatant and maintaining the catalytic activity of the proteins. More specifically the method comprises that the liquid phase (supernatant) from a single cell oil production process is treated by at least one method enriching the proteins in the liquid phase. The protein fraction is enriched at least 10%, typically at least 20%, in various embodiments at least 30%, at least 40%, at least 50%, at least 60%, at least 70%, at least 80%, at least 90%, compared to the original liquid phase. Examples of suitable methods are methods based on ionic properties of proteins, molecule size, solubility, surface active properties or hydrophobic interactions. Preferably the recovery of enzyme fraction is carried out under conditions, where the temperature is 70° C. or lower.

"Cellulase" or "cellulolytic enzyme" refers to a group of enzymes produced mainly by fungi, such as filamentous fungi or yeasts, bacteria, plants of by animals that catalyze the hydrolysis of cellulose, also called as cellulolysis. The EC number for cellulase enzymes is EC 3.2.1.4. Several different kinds of cellulases are known, which differ structurally and mechanistically. The general of cellulases include, based on the type of reaction catalyzed, endo-cellulases, exo-cellulases, cellobiases or beta-glucosidases, oxidative cellulases, and cellulose phosphorylases.

"Hemicellulase" refers to a group of enzymes produced mainly by fungi, such as filamentous fungi or yeasts, bacteria, plants of by animals that catalyze the hydrolysis of hemicellulose. For example, the enzymes involved in the hydrolysis of xylan include endo-xylanases, acetyl-xylanesterases, α-D-glucuronidases, α-L-arabinofuranosidases, ferulic acid esterases and β-Xylosidases. In addition, the enzymes involved in the hydrolysis of galactoglucomannan include endo-mannanases, acetyl-mannanesterases, α-Galactosidases, β-Glucosidases, β-Mannosidases. In addition the enzymes involved in the hydrolysis of arabinogalactan include β-Galactosidase and Endo-α-L-arabinanase. These enzymes can be found under the following EC numbers: EC 3.2.1.8, EC 3.2.1.37, EC 3.2.1.55, EC 3.2.1.99, EC 3.2.1.139, EC 3.2.1.78, EC 3.2.1.25, EC 3.2.1.22, EC 3.2.1.21, EC 3.2.1.89, EC 3.1.1.72, EC 3.1.1.6, EC 3.1.1.73.

"Hemicellulose" refers to a group of complex carbohydrates found in a lignocellulosic material that, with other carbohydrates (e.g., pectins), surround the cellulose fibres of plant cells. The composition of hemicelluloses is dependent on the plant type. Most common types of hemicelluloses include xylan, glucoronoxylan, glucomannan, galactoglucomannan, arabinoxylan, xyloglucan and arabinogalactan.

"Lignocellulosic material" or "lignocellulosic biomass" refers to biomass that is composed of cellulose, hemicellulose, and lignin.

"Saccharification" refers as hydrolysis of polymeric sugars to sugar monomers. Saccharification is typically achieved by the use of enzymes capable if hydrolysing polymeric sugars.

"Oleaginous microorganism" refers here as a microorganism which is capable of accumulating at least 15% (w/w) lipids of their biomass when cultivated in suitable or optimal-cultivation conditions.

"Pulp and paper industry primary sludge" refers to a sludge generated in the primary treatmend of waste water from pulp and/or paper industry process. Primary sludge consists of suspended material in pulp and paper industry waste water typically contain oligomeric cellulose, hemicellulose and lignin and/or inorganic compounds. Typically, primary sludge is obtained by sedimentation (clarification, settling) of suspended material is wastewater. In addition to sedimentation, other methods can be used to collect suspended material from pulp and paper waste water. This is considered a primary treatment of the waste water and the solids produced are known as primary sludge.

Cellulose does not typically dissolve in water in nature. The hydrolysis of solid cellulose requires three different types of enzymes. Endoglucanases, exoglucanases and β-glucosidases Endoglucanases (EC 3.2.1.4), operated mostly on amorphous part of cellulose, attacking randomly on internal ponds of cellulose macromolecule. Exo-glucanases or cellobiohydrolases (EC 3.2.1.91) attacks on the end of cellulose chain hydrolyzing mainly one cellobiose unit at a time. Exo-glucanases are able also to hydrolyse chrystalline cellulose polymer. Finally, the hydrolysis of cellobiose to glucose monomers is done by β-glucosidase (EC 3.2.1.21).

Cellulose hydrolysis needs co-operation of many different cellulases. The amount of different analysed glycosylhydrolases is very high, over 90 different enzymes are already numbered (even more under study) on 14 different families as example cellobiohydrolase domains (CBH I, II), endoglucanese domains (EG I, II, III, IV, V) and betaglucosidase domains (BGL I, II). In many applications of enzymes in pulp and paper industry, such as in pulp (pre)bleaching, the degradation cellulose fibres by cellulases is unfavourable.

For the total enzymatic hydrolysis of hemicellulose (xylans, arabinoxylans and glucomannans) several different enzymes are needed, which must be activated about the same time. First attack is done by enzymes such as endoxylanases (1,4-β-D-xylan xylanohydrolases), endoarabinases, and endomannanases (1,4-β-D-mannan mananohydrolases). For example Trichoderma reesei has at least 4 different endo-xylanases and one endo-mannanase.

Enzymes capable to hydrolyse hemicellulose oligomers after endo-hemicellulases operation are β-xylosidase, β-arabinosidase, β-mannosidase and β-glucosidase (EC 33.2.1.21). For braking down the residual side-linkages included in oligomers α-glucuronidase (EC 3.2.1.139), α-arabinodase (EC 3.2.1.55) and α-D-galactosidase (EC. 3.2.1.22) are needed. For removal of acetyl-constituents is needed operation of esterases (EC 3.2.1.72).

Further, enzymatic hydrolysis of lignin requires activity of oxidative enzymes such as lignin peroxidase (LiP EC 1.11.1.14), manganese-dependent peroxidase (MnP EC 1.11.1.13) and laccase (Ec 1.10.3.2). Modification of lignin needs co-operation of many enzymes, coenzymes and electron transport system between donors and final acceptors. The chemical structure and attachment of lignin to cellulose and hemicellulose is more important than the amount of lignin.

The spent culture medium (effluent) from lipid production process or cell residues (residual biomass) from lipid recovery process from which enzymes have been recovered can be used for several purposes. It can be, e.g. recycled partly or entirely to lipid production process. Alternatively, it can be treated in the waste water treatment plant in pulp and paper industry. The effluent and/or biomass residue contains nutrients that can decrease the need of nutrient addition to pulp and/or paper waste water treatment process. The spent culture medium and/or cell residues can be also treated in anaerobic digestion biogas to biogas with or without supplementation of pulp and/or paper production residues or sludge from pulp and/or paper process waste water treatment. The sludge from anaerobic digestion can be potentially used as a fertilizer.

ILLUSTRATED EMBODIMENTS

In summary, various embodiments of the invention are described below with the aid of the following numbered clauses 1-31. The embodiments are illustrative and are not intended to limit the claimed subject matter.

Clauses

1. An integrated process comprising
   a first process, which is a single cell oil production process, and a second process, which is a pulp and/or paper industry process,
   wherein organic material from pulp and/or paper industry is introduced into the single cell oil production process, and wherein in the single cell oil production process is used a microorganism capable of producing lipids or lipids and enzymes when cultivated on a medium comprising organic material from pulp and/or paper industry,
      producing lipids or lipids and enzymes by said microorganisms in the single cell oil production process and/or in a process connected into it,
      separating supernatant and/or microorganism cells from the microorganism culture,
      recovering lipids from the microorganism cells, and
   recovering the supernatant or a protein enriched fraction of the supernatant or a dilution of the supernatant comprising catalytically active enzymes from the single cell oil production process or from a process connected to it and optionally introducing it or them into the pulp and/or paper industry process.
2. The process according to clause 1, wherein at least 5% of certain enzyme(s) used in the pulp and/or paper industry process are produced in the single cell oil production process or in a process connected to the process.
3. The process according to clause 1 or 2, wherein the enzymes and lipids are produced by the same microorganism.
4. The process according to any one of clauses 1 to 3, wherein the enzymes and lipids are produced by one or more microorganisms.
5. The process according to any one of clauses 1 to 4, wherein the enzymes producing microorganism and the lipid producing microorganism are different.
6. The process according to any one of clauses 1 to 5, wherein the enzymes are produced in a separate process from the single cell oil production process integrated into pulp and/or paper industry process.
7. The process according to any one of clauses 1 to 6, wherein the enzymes comprises hemicellulases, xylanases, mannanases, galatosidases, peroxidases, laccases, pectinases, cellulases, glucosidases, arabinases, lipases, amylases, esterases or proteases or any mixtures thereof.
8. The process according to any one of clauses 1 to 7, wherein the organic material fed to the single cell oil production process comprises at least 50% lignocelluloses or a fraction of lignocellulose, preferably at least 10% polymeric sugars.
9. The process according to any one of clauses 1 to 8, wherein the organic material comprises at least 20%, preferably at least 30% hemicelluloses, or fraction(s) of hemicellulose.
10. The process according to clause 8 or 9, wherein the organic material comprises hemicellulose or a fraction thereof from dissolving pulp process or extracted prior to cooking in Kraft pulp process or in dissolving pulp process.
11. The process according to any one of clauses 1 to 10, wherein the enzymes comprise exoenzymes, preferably enzymes associated with hemicellulose hydrolysis.
12. The process according to clause 11, wherein the enzymes comprise hemicellulases, xylanases, mannanases, arabinases, galactosidases, glucosidases, mannosidases, xylosidases, arabinofuranosidases or esterases or any mixtures thereof.
13. The process according to any one of clauses 1 to 12, wherein the organic material comprises at least 20% cellulose, preferably at least 30% cellulose or fractions thereof.
14. The process according to any one of clauses 1 to 13, wherein the organic material is primary sludge and/or fibre waste from pulp and/or paper industry.
15. The process according to any one of clauses 1 to 14, wherein the enzymes comprise exoenzymes, preferably enzymes associated with cellulose hydrolysis.
16. The process according to any one of clauses 1 to 15, wherein the enzymes comprise cellulases, endo-cellulases, exo-cellulases, cellobiases or beta-glucosidases, oxidative cellulases, cellulose phosphorylase or hemicellulases or any mixtures thereof.
17. The process according to any one of clauses 1 to 16, wherein both cellulases and hemicellulases are produced.
18. The process according to any one of clauses 1 to 16, wherein the hydrolysis products of polymeric sugars from pulp and/or paper industry process are recirculated into the lipid production process.
19. The process according to any one of clauses 1 to 17, wherein the pulp and/or paper industry process comprises a process, such as a dissolving pulp process, treatment of lignocellulose in or prior to pulping (enhancing dissolving pulping), Kraft pulp process, treatment of lignocellulose in or prior to pulping (enhancing Kraft-pulping), pulp (pre) bleaching, or mechanical pulp process, fibre modification, debarking, recycle fibre process, deinking, fibre modification, papermaking, or slime and/or pitch removal.
20. The process according to any one of clauses 1 to 19 wherein the microorganism is a filamentous fungus, yeast or a bacterium, preferably a fungus belonging to a genus selected from the group of *Aspergillus, Humicola, Rhizopus,* and *Trichoderma,* or a yeast belonging to genus *Cryptococcus,* or a bacterium belonging to the genus *Streptomyces.*
21. An enzyme preparation obtained by the process according to any one of clauses 1 to 19.
22. Use of the enzyme produced according to the process of any one of clauses 1-19 or the enzyme preparation according to clause 21 in pulp and/or paper industry or in other application as an enzyme preparation or as a source of enzymes.
23. Use of the hemicellulases produced according to the process of any one of clauses 1 to 20 or enzyme preparation according to clause 21 in pulp (pre)bleaching, enhancing 23. dissolving pulp process, enhancing Kraft pulp process, debarking, deinking and/or fibre modification, preferably in (pre)bleaching.
24. Use of cellulases produced according to the process of any one of clauses 1-20 or enzyme preparation according to clause 21 in deinking, fibre modification, enhancing dissolving pulp process, enhancing Kraft pulp process and/or debarking, preferably in fibre modification and/or deinking.
25. An integrated process system for lipid production and pulp and/or paper industry, which comprises that the lipid production process uses organic material from pulp and/or paper industry as raw material for lipid production, and a pulp and/or paper process uses enzymes from supernatant from lipid production process
26. An integrated process system for lipid production and chemical pulping process, which comprises that the lipid production process uses hemicellulose, primary sludge and/or fractions thereof as raw material for lipid production, and pulp and/or paper process uses hemicellulases obtained from lipid production process.
27. An integrated process system for of lipid production and recycle fibre process, which comprises that the lipid production process uses deinking sludge and/or fractions thereof as raw material for lipid production, and pulp and/or paper process uses enzymes obtained from lipid production process.
28. An integrated process system for lipid production and mechanical pulping process, which comprises that the lipid production process uses residues from mechanical pulping, primary sludge and/or fractions thereof as raw material for lipid production, and pulp and/or paper process uses enzymes obtained from lipid production process.
29. A process for producing lipids, which comprises
    cultivating a microorganism capable of producing both lipids and enzymes under conditions suitable for lipid production and enzyme production on a medium comprising organic material from pulp and/or paper industry, and producing lipids and enzymes by said microorganisms,
    separating the supernatant and microorganism cells from the microorganism culture,
    recovering lipids from the microorganism cells, and
    recovering the supernatant or a protein enriched fraction of the supernatant or a dilution of the supernatant comprising catalytically active enzymes.
30. Use of the lipids produced according to the process of any one of clauses 1 to 20 or the enzyme preparation according to clause 21 as biofuel as a component of biofuel or as a starting material for biofuel production.
31. The use according to clause 30, wherein the biofuel is biodiesel or renewable diesel, gasoline and/or jet fuel.

It is an object of the following examples to illustrate the invention and shall not be construed as limiting the invention in any way.

EXAMPLES

The enzyme activities in spent culture broth from cultivations of fat-producing filamentous fungi were determined by hydrolysis tests with pure cellulose and xylan as substrates.
Methods
Sugar Definition:
In order to define the sugar concentration of a solution, the solution was made into a suitable dilution which was filtered through 0.2 µm prior to an HPLC analysis.

The column used in sugar definition was Shodex Sugar SP 0810 ion-exchanger in lead form (in stationary phase). The column dimensions were 8.0 mm (ID)×300 mm. The eluent was water (flow rate 0.6 ml/min) and the column temperature was 60° C. The detector was RI Shimatzu RID 10A and the pump was A6 and the autosampler was Shimatzu SIL 20A. The processing of results was conducted with Class-VP software.
Fatty Acid Analysis:
The fatty acid composition of samples was determined as in the method described by Suutari et al., (1990). Lipids in the samples were first hydrolyzed into free fatty acids, which were saponified into sodium salts thereof and thereafter methylated into methyl esters. The fatty acid methyl esters were analyzed gas chromatographically.
Protein Concentration Analysis:
The protein concentration of the culture broths were analysed after filtration of the broth through Whatman3 filterpaper. The protein concentration was analysed according to the Bio-Rad Protein Assay (based on Bradford method).
Hydrolysis Tests:
The culture broth was filtered through Whatman3 filterpaper before the hydrolysis test.
The xylanase activity was determined as follows. A 100 ml Erlenmeyer flask was used as the reaction vessel. It was filled with 20 ml 1% birch wood xylan (Sigma) solution in phosphate buffer (0.02 M, pH 5) as substrate, 10 ml filtered culture broth and 20 ml phosphate buffer (0.02 M, pH 5). The hydrolysis reaction was performed in an agitated (140 rpm) water bath at 50° C. Samples of 1 ml were taken from the reaction vessel directly after the addition of the culture broth and after 1, 3, 5, 21/23 hours. The hydrolysis reaction was stopped in the 1 ml sample by decreasing the pH by the addition of 50 µl of 1.33 M sulphuric acid. Samples were treated for salt and polymeric sugar removal to suit HPLC-analysis. The released sugars were analysed by HPLC (see Sugar definition) with mannitol as standard.

Cellulase activity was determined with 1 g Whatman filterpaper as cellulose substrate instead of xylan. The reaction volume was 50 ml containing 1 g Whatman filterpaper in equal sized circles (ca. 5 mm diameter) as substrate, 10 ml filtered culture broth and 40 ml phosphate buffer (0.02 M, pH 5). The experiment was otherwise performed as with xylan.
Microorganism Strains:
Lipid producing microorganisms are generally available to the public from a plurality of recognized microbial culture (strain) collections, such as ATCC, DSM, etc. Various embodiments of the invention are discussed in the following examples by using microorganism strains as follows. *Aspergillus oryzae* DSM 1861, *Aspergillus oryzae* DSM 1864 and *Aspergillus terreus* DSM 1958.

Example 1

This example shows the enzymatic activity formed in the culture broth during the cultivation of *Aspergillus oryzae* with hemicellulose based material as carbon source for the production of lipids.

*Aspergillus oryzae* was grown in flask cultures with purified birch xylan (Sigma) and spruce and birch hemicelluloses extracted with pressurized hot water extraction as carbon source. Cultivations were done in 250 ml Erlenmeyer flasks containing 50 ml culture medium. The growth medium base contained per liter of water 1 g $(NH_4)_2SO_4$, 1 g $MgSO_4 \cdot 7H_2O$, 0.5 g $K_2HPO_4$, 1 g $KH_2PO_4$ and 0.2 g $CaCl_2 \cdot 2H_2O$ and was supplemented with carbon source, yeast extract and optionally support material. Cultivation media were inoculated with 1% (v/v) fungal spore suspension and the cultures were incubated at 28° C. temperature.

In the case of purified xylan the medium base was supplemented with per liter 40 g purified birch xylan (Sigma) and 1 g yeast extract. Duplicate cultivations were incubated in orbital shaker (160 rpm) for 6 days.

In the case of spruce and birch hemicellulose the medium base was supplemented with per liter 44 g of dried spruce or birch hemicellulose produced by hot water extraction, 0.5 g yeast extract and 2 g cellulose to give mechanical support for the fungal mycelium. Triplicate cultivations were incubated in orbital shaker (180 rpm) for 7 days.

After incubation the culture broth was filtered through Whatman 3 filterpaper. Protein concentration and enzyme activities were determined from the filtrate. The retentate was washed with distilled water and dried. Biomass concentration and lipid content were determined from the dried samples.

On purified birch xylan after 6 d cultivation *A. oryzae* fungus produced 16 g/l biomass (dry weight) and the biomass contained 10.5% lipids/dry weight. *Aspergillus oryzae* grown on water extracted birch hemicellulose produced 14 g/l dry biomass during 7 d incubation. The biomass containing fungal mycelium, residual hemicellulose and cellulose contained 8.9% lipids/dry weight equaling to 1.26 lipids per liter of cultivation medium. For lipid production both birch xylan and hemicellulose were better than spruce hemicellulose as on spruce hemicellulose 8.7 g/l dry biomass containing 3.7% lipids/dry weight was produced.

The protein concentration of the culture broths were 0.06 and 0.02 mg/ml for the spruce and birch hemicellulose cultivations and 0.05 mg/ml for the birch xylan cultivation.

Figure 3:
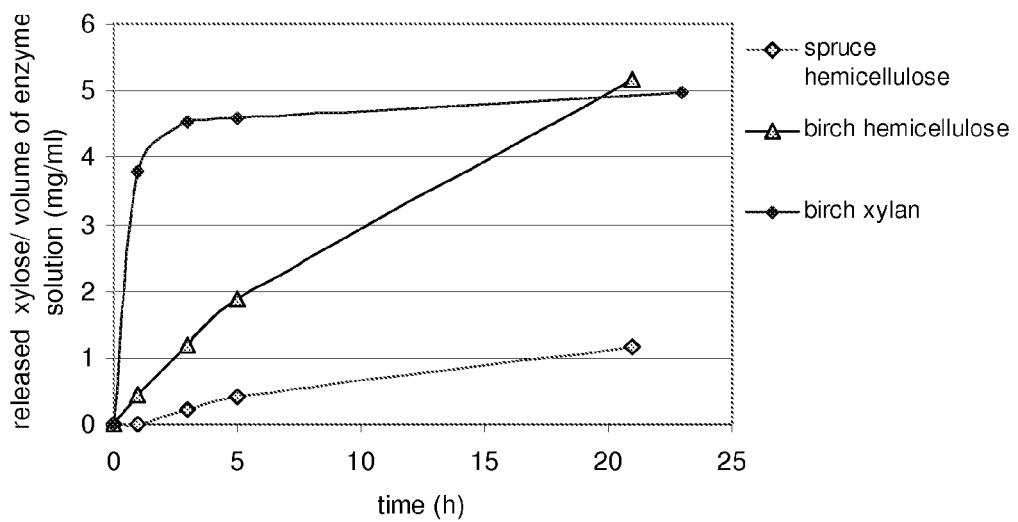
FIG. 3 shows the xylose released in the hydrolysis test per volume of culture broth. As substrate was used 200 mg birch wood xylan.
Figure 4:
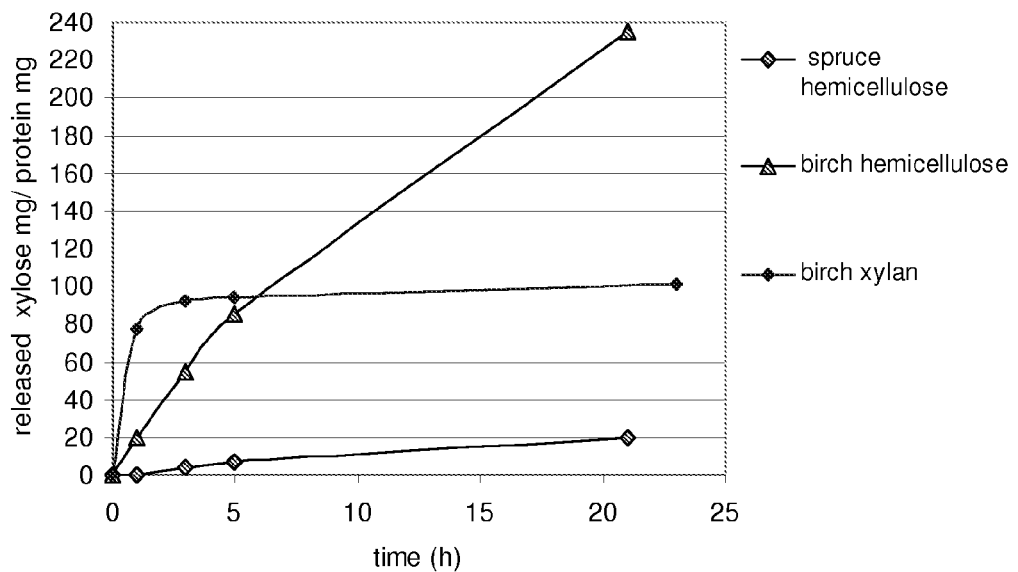
FIG. 4 shows the xylose released in the hydrolysis test per protein. As substrate was used 200 mg birch wood xylan.

The released xylose from the xylan hydrolysis test as a function of time per milliliter culture broth and per milligram of protein in the reaction is presented in 3 and 4. In FIG. 3 is shown the xylose released in the hydrolysis test per volume of culture broth. As substrate was used 200 mg birch wood xylan. In FIG. 4 is shown the xylose released in the hydrolysis test per protein. As substrate was used 200 mg birch wood xylan.

One milliliter of culture broth from the spruce hemicellulose cultivation released 1.2 mg of xylose in 21 h and 20.1 mg/mg protein. One milliliter of culture broth from the birch hemicellulose cultivation released 5.2 mg of xylose in 21 h and 234.6 mg/mg protein. One milliliter of culture broth from the birch xylan cultivation released 5.0 mg of xylose in 23 h and 101.4 mg/mg protein.

The culture broths from *Aspergillus oryzae*-cultivations with hemicellulose or xylan carbon source showed significant xylanase activity. The culture broths had no detectable cellulase activity as no free glucose was detected in the cellulose hydrolysis test. The examples indicate that spend culture medium from lipid production with *A. oryzae* from wood hemicellulose hydrolysates contains hemicellulases, such as xylanases, which can be in the degradation of hemicellulose of wood materials which is a favourable property for pulp (pre)bleaching. Lipid production from hemicellulose from wood material shows an example of an integration possibility of lipid production process to a Kraft-pulp process or a dissolving pulp process with hemicellulose pre-extraction step. Further, the activity of hemicellulases, but lack of cellulase activity, indicates the applicability of the enzymes for pulp (pre)bleaching applications.

Example 2

This example shows the selective xylanase activity formed in the culture broth during the cultivation of *Aspergillus oryzae* with lignocellulose based material as carbon source for the production of lipids.

*Aspergillus oryzae* was cultured for lipid production on cellulose based lignocellulose materials. The growth medium base contained per liter of water 40 g lignocellulosic material as carbon source, 1.46 g peptone as nitrogen source, 0.5 g yeast extract, 1 g $MgSO_4.7H_2O$, 0.5 g $K_2HPO_4$, 1 g $KH_2PO_4$ and 0.2 g $CaCl_2.2H_2O$, 0.00015 g $ZnSO_4.7H_2O$, 0.0001 g $CuCl.2H_2O$ and 0.00625 g $MnCl_2.4H_2O$. The carbon source was milled and sieved (0.2 mm) bleached birch hardwood sulphate cellulose containing ca. 15% hemicellulose. This cellulose material was added to the cultivation to give a final concentration of 50 g/l. The cultivation medium was inoculated with 50 ml 48 h precultured *Aspergillus oryzae* suspension. The fermentation was performed in 1 L culture medium volume at 28° C. temperature with 0.8 l/min aeration and 350-450 rpm agitation. Culture pH was 5.7 and it was adjusted with 3 M NaOH during the cultivation. Enzyme activities were determined after 188 h incubation.

Figure 5:
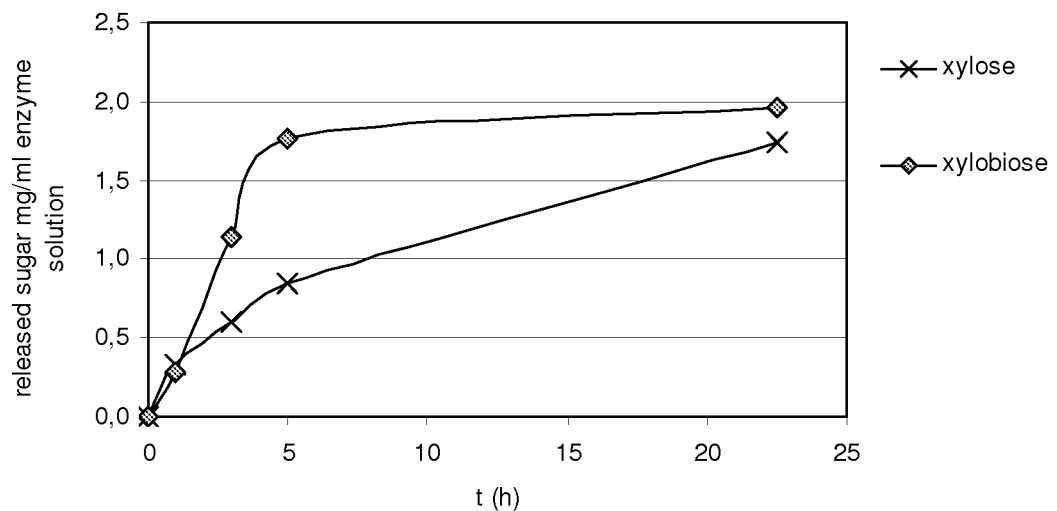
FIG. 5 shows the xylose and xylobiose released in the hydrolysis test per volume of culture broth. As substrate was used 200 mg birch wood xylan.
Figure 6:
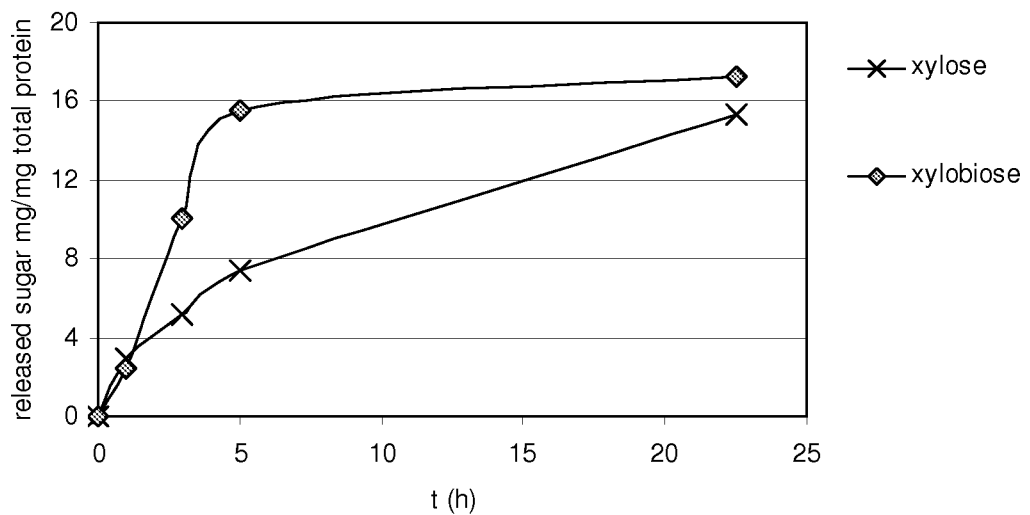
FIG. 6 shows the xylose and xylobiose released in the hydrolysis test per protein. As substrate was used 200 mg birch wood xylan.
Figure 7:
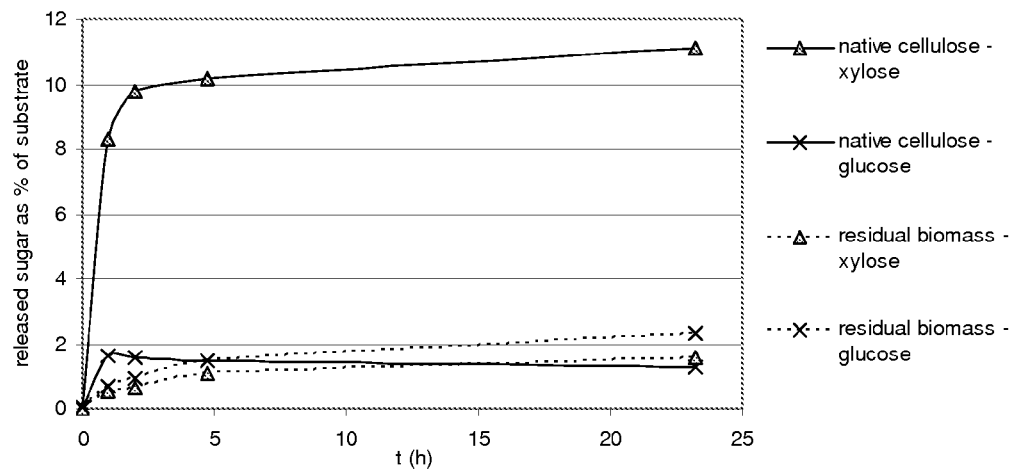
FIG. 7 shows the released sugar (xylose and glucose) as % of substrate (500 mg native cellulose or residual biomass from cultivation) during the hydrolysis test with 1 ml commercial xylanase solution.

The cultures broths were separated and the protein concentration and the xylanase and cellulase activity assayed as described above. The protein concentration in the culture broth was 0.11 mg/ml. The sugar released during the hydrolysis tests as milligram per milliliter culture broth and milligram per milligram protein as a function of time is presented in FIGS. 5 and 6. FIG. 5 shows the xylose and xylobiose released in the hydrolysis test per volume of culture broth. As substrate was used 200 mg birch wood xylan. FIG. 6 shows the xylose and xylobiose released in the hydrolysis test per protein. As substrate was used 200 mg birch wood xylan. FIG. 7 shows the released sugar (xylose and glucose) as % of substrate (500 mg native cellulose or residual biomass from cultivation) during the hydrolysis test with 1 ml commercial xylanase solution.

A significant amount of residual cellulosic material was left after 188 h cultivation. This biomass was treated with commercial xylanase (protein 10.6 mg/ml) in order to determine the composition of the residue. As a reference native birch cellulose was treated with the same enzyme solution. In the hydrolysis tests 500 mg dried cellulose material was suspended in 49 ml phosphate buffer (0.02 M, pH 5) and 1 ml enzyme solution. The hydrolysis test was otherwise performed similarly as the enzyme activity assays. The sugar released during the hydrolysis tests as milligram per milliliter culture broth and milligram per milligram protein as a function of time is presented in FIG. 7.

The enzyme assay (cellulase and xylanase) for the culture broth showed only xylanase activity but no cellulase activity was detected. In the hydrolysis test with xylan as substrate, significant amounts of both xylose and xylobiose was released.

The hydrolysis test with the commercial xylanase (with small cellulase activity) for the residual biomass showed that only traces of hemicellulose (less than 2% xylose released) could be hydrolyzed from the residual cellulose from the cultivation. In other words, the xylanase formed to the broth during the cultivation had effectively hydrolyzed the hemicellulose part of the cellulose.

From the original native cellulose material used in the cultivation as carbon source 11% of the substrate was released as xylose when treated with xylanase. The material contained ca. 15% hemicelluloses.

This example shows that *Aspergillus oryzae* can produce enzymes with selective xylanase activity (no cellulase activity) in lipid production process when cultured with lignocellulose material as carbon source. This xylanase can be used to selectively hydrolyse hemicellulose leaving an enriched cellulose fraction intact. The activity of hemicellulases, but lack of cellulase activity, indicates the applicability of the enzymes in pulp (pre)bleaching applications.

Example 3

This example shows the enzymatic activity formed in the culture broth during the cultivation of *Aspergillus terreus* with hemicellulose based material as carbon source for the production of lipids.

*Aspergillus terreus* was cultivated for lipid production on a wheat straw hemicellulose as carbon substrate in 2 liter volume in a bioreactor. The culture medium comprised of 50 ml Yeast Nitrogen Base w/o Amino Acids and Ammonium sulphate (Difco) 10× stock solution suspended in 2 L water and supplemented with per liter: 1.0 g yeast extract, 1 g $(NH_4)_2SO_4$, 1 g $MgSO_4.7H_2O$, 0.5 g $K_2HPO_4$, 1 g $KH_2PO_4$, 0.2 g $CaCl_2.2H_2O$ and 2 g cellulose. The culture medium was inoculated with 150 ml 24 h precultured *A. terreus* culture. The fermentation was performed at 35° C. temperature with 3.0 l/min aeration and 200-430 rpm agitation. Culture pH was 5.7 and it was adjusted with 3 M NaOH during the cultivation. During the cultivation hemicellulose solution was fed to the fermentor. Enzyme activities were determined after 165 h incubation.

The culture broth was separated and it was partly concentrated by ultrafiltration in an Amicon stirred ultrafiltration cell with a 10 000 Da filter (Millipore). The protein and lipid concentration and the xylanase and cellulase activity were assayed as described as above.

The lipid content in the biomass containing fungal mycelium, residual hemicellulose and cellulose was 15% per dry weight. The protein concentration was 0.72 mg/ml in the unconcentrated culture broth and 2.15 mg/ml in the concentrated broth.

The sugar released during the hydrolysis tests as milligram per milliliter culture broth and milligram per milligram protein as a function of time is presented in FIGS. 8 to 11.

Figure 8:
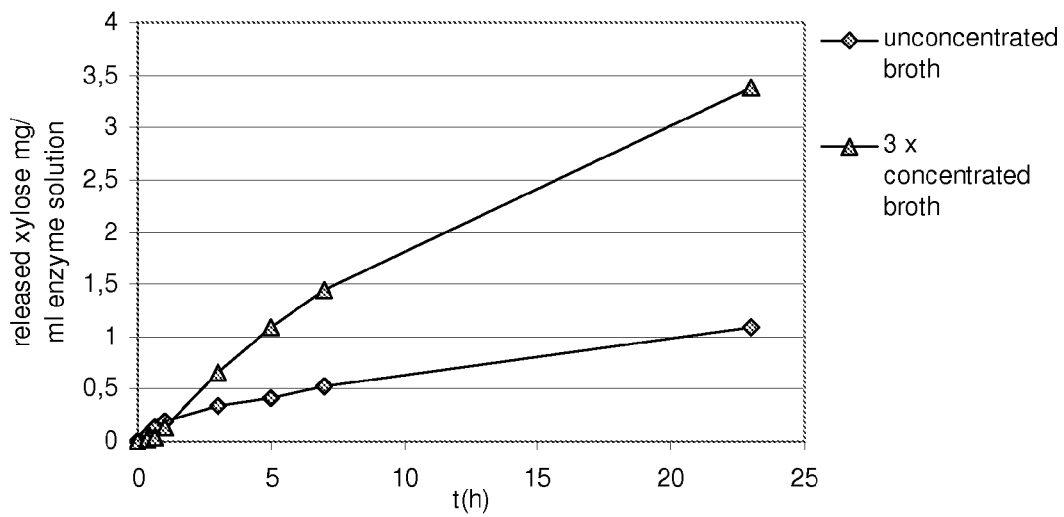
FIG. 8 shows the xylose released in the hydrolysis test per volume of culture broth. As substrate was used 200 mg birch wood xylan.
Figure 9:
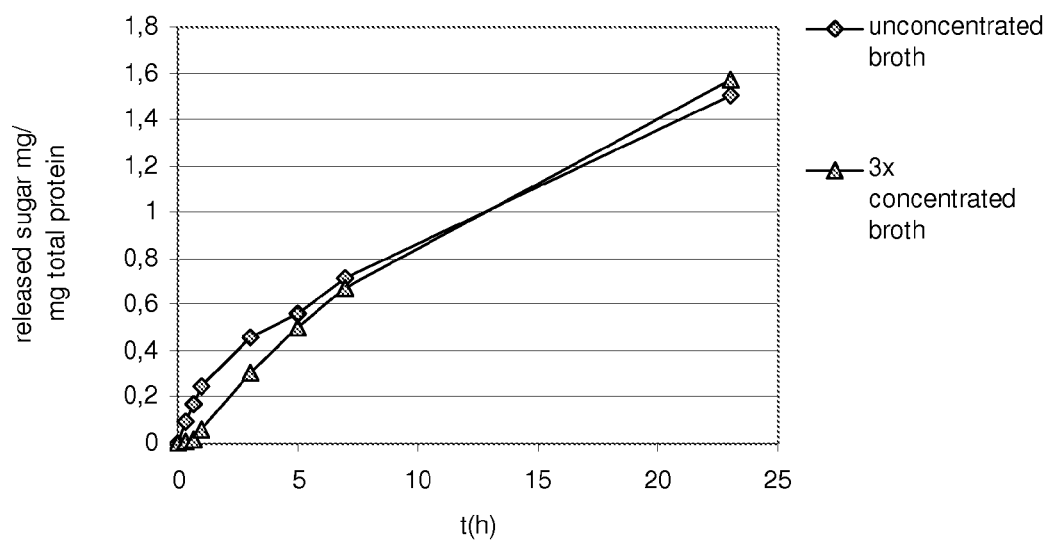
FIG. 9 shows the xylose released in the hydrolysis test per protein. As substrate was used 200 mg birch wood xylan.
Figure 10:
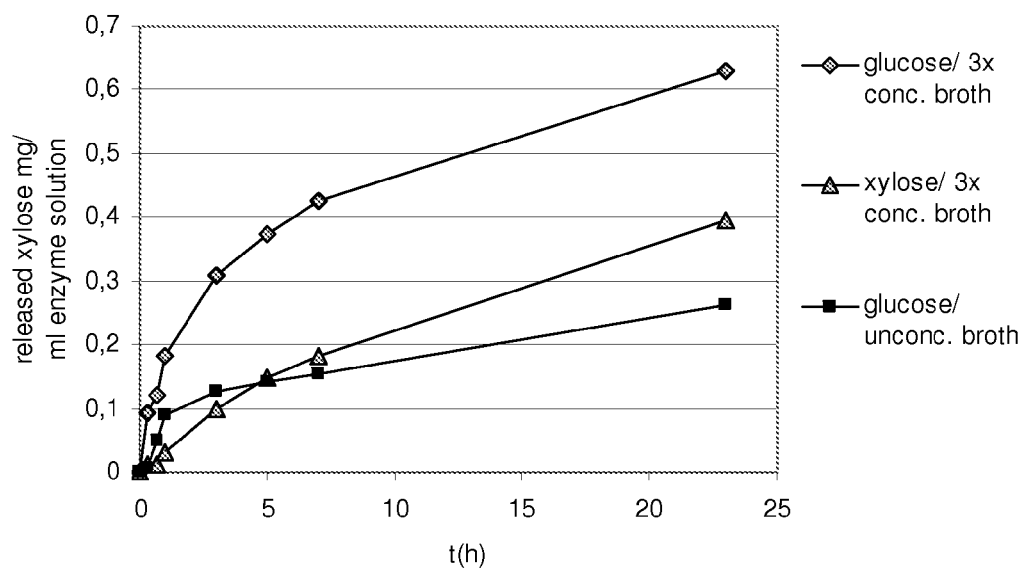
FIG. 10 shows the glucose released in hydrolysis tests per volume of culture broth. As substrate was used 1 g cellulose. Some xylose was released from the hemicellulose originating from the culture broth used.
Figure 11:
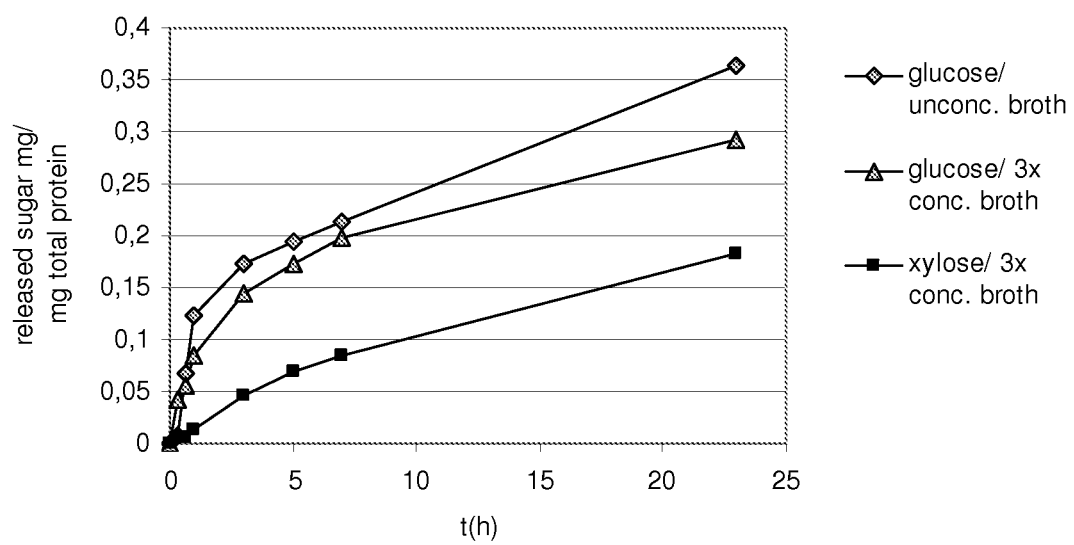
FIG. 11 shows the glucose released in the hydrolysis test per protein. As substrate was used 1 g cellulose. Some xylose was released from the hemicellulose originating from the culture broth used.

FIG. 8 shows the xylose released in the hydrolysis test per volume of culture broth. As substrate was used 200 mg birch wood xylan. FIG. 9 shows the xylose released in the hydrolysis test per protein. As substrate was used 200 mg birch wood xylan. FIG. 10 shows the glucose released in hydrolysis tests per volume of culture broth. As substrate was used 1 g cellulose. Some xylose was released from the hemicellulose originating from the culture broth used. FIG. 11 shows the glucose released in the hydrolysis test per protein. As substrate was used 1 g cellulose. Some xylose was released from the hemicellulose originating from the culture broth used.

This example indicates that *Aspergillus terreus* can produce both intracellular lipids and extracellular hydrolytic enzymes to the culture broth. The example shows that *A. terreus* produces and excretes to growth medium enzymes that have both xylan and cellulose degradation activity. These enzymes can be separated, concentrated and used in hydrolysis and treatment of lignocellulosic material in applications were both cellulase and hemicellulose activities are favorable. Such applications in pulp and/or paper industry may include such as fiber modification, deinking or debarking. Further, the strain for activity of towards both polymeric cellulose and hemicellulose is applicable for use with pulp and/or paper industry residues containing both cellulose and hemicellulose, such as primary sludge from deinking, chemical pulping and/or mechanical pulping. Therefore this example indicates a possibility of integrating lipid production process with chemical pulping, mechanical pulping or fibre recycling processes.

REFERENCES

Bajpai P. 2004. Biological Bleaching of Chemical Pulps. Critical Reviews in Biotechnology. 24:1-58.
Beg Q K, Kapoor M, Mahajan L, Hoondal G S. 2001. Microbial xylanases and their industrial applications: a review. Appl Microbial Biotechnol (2001) 56:326-338.
Dhiman S S, Sharma J, Battan B. 2008. Industrial application and future prospects of microbial xylanases: a review. Bioresources 3:1377-1402.
Fall R, Phelps P, Spindler D. 1984. Bioconversion of Xylan to Triglycerides by Oil-Rich Yeasts. Applied and Environmental Microbiology 47:1130-1134.
Lin H, Cheng W, Ding H T, Chen X J, Zhou Q F, Zhao Y H. 2010. Direct microbial conversion of wheat straw into lipid by a cellulolytic fungus of *Aspergillus oryzae* A-4 in solid-state fermentation. Bioresource Technology 101:7556-7562.
Lynd L R, van Zyl W H, McBride J E, Laser M. 2005. Consolidated bioprocessing of cellulosic biomass: an update. Current Opinion in Biotechnology 16:577-583.
Huang H-J. Ramaswamy S, Tschirner U W, Ramarao B V. 2008. A review of separation technologies in current and future biorefineries. Separation and Purification Technology 62:1-21.
Marinova M, Mateos-Espejel E Jemaa N, Paris J. 2009. Addressing the increased energy demand of a Kraft mill biorefinery: The hemicellulose extraction case. Chemical engineering research and design 87:1269-1275.
C. V. T. Mendes, M. G. V. S. Carvalho C. M. S. G. Baptista, J. M. S. Rocha, B. I. G. Soares, G. D. A. Sousa. 2009. Valorisation of hardwood hemicelluloses in the kraft pulping process by using an integrated biorefinery concept. Food and Bioproducts Processing 87:197-207.
Suutari M, Liukkonen K, Laakso S. 1990. Temperature adaptation in yeasts: the role of fatty acids. Journal of General Microbiology 136: 1469-1474.

The invention claimed is:

1. An integrated process for single cell oil production and a pulp and/or paper industry process, the integrated process comprising:
   (a) cultivating a microorganism in a culture medium comprising organic material from a pulp or paper industry process, wherein the microorganism produces lipids and enzymes capable of degrading wood material or organic material from a pulp or paper industry process;
   (b) extracting the lipids and the enzymes from cells of the microorganism or from the culture medium; and
   (c) performing a pulp and/or paper industry process that comprises treating wood material or organic material with the enzymes.

2. The process according to claim 1, wherein the pulp and/or paper industry process is a chemical pulping process, and wherein the single cell oil production process uses hemicellulose, primary sludge and/or fractions thereof as raw material for single cell oil production, and the pulp and/or paper industry process uses hemicellulases obtained from the single cell oil production process.

3. The process according to claim 1, wherein the pulp and/or paper industry process is a recycle fibre process, and wherein the single cell oil production process uses deinking sludge and/or fractions thereof as raw material for single cell oil production, and the pulp and/or paper industry process uses enzymes obtained from said single cell oil production process.

4. The process according to claim 1, wherein the pulp and/or paper industry process is a mechanical pulping process, and wherein the single cell oil production process uses residues from mechanical pulping, primary sludge and/or fractions thereof as raw material for single cell oil production, and the pulp and/or paper industry process uses enzymes obtained from said single cell oil production process.

5. The process according to claim 1, wherein the enzymes comprise hemicellulases, xylanases, mannanases, galactosidases, peroxidases, laccases, pectinases, cellulases, glucosidases, arabinases, lipases, amylases, esterases or proteases or any mixtures thereof.

6. The process according to claim 1, wherein the organic material fed to the single cell oil production process comprises at least 50% lignocelluloses or a fraction of lignocellulose.

7. The process according to claim 1, wherein the organic material comprises at least 20% hemicelluloses, or fraction(s) of hemicellulose or at least 20% cellulose, or fractions thereof.

8. The process according to claim 1, wherein the enzymes comprise exoenzymes.

9. The process according to claim 1, wherein the pulp and/or paper industry process comprises a dissolving pulp process, Kraft-pulp process, pulp (pre)bleaching, or mechanical pulp process, fibre modification, debarking, recycle fibre process, deinking, fibre modification, papermaking, or slime and/or pitch removal.

10. The process according to claim 1, wherein the microorganism is a filamentous fungus, yeast or a bacterium.

11. The process according to claim 6, wherein the organic material comprises at least 10% polymeric sugars.

12. The process according to claim 7, wherein the organic material comprises at least 30% hemicelluloses or fractions of hemicellulose or at least 30% cellulose or fractions of cellulose.

13. The process according to claim 8, wherein the enzymes comprise enzymes associated with hemicellulose hydrolysis or cellulose hydrolysis.

14. The process according to claim 10, wherein the microorganism is a fungus belonging to a genus selected from the group of *Aspergillus, Humicola, Rhizopus*, and *Trichoderma*.

15. The process according to claim 10, wherein the microorganism is a yeast belonging to genus *Cryptococcus*.

16. The process according to claim 10, wherein the microorganism is a bacterium belonging to genus *Streptomyces*.

17. The process according to claim 1, further comprising transesterifying the lipids.

\* \* \* \* \*